US007696243B2

(12) United States Patent
Araldi

(10) Patent No.: US 7,696,243 B2
(45) Date of Patent: Apr. 13, 2010

(54) PYRROLIDIN-2-ONE DERIVATIVES FOR USE AS DP$_1$ RECEPTOR AGONISTS

(75) Inventor: Gian Luca Araldi, Sedauket, NY (US)

(73) Assignee: Merck Serono, S.A., Coinsins, Vaud (CH)

( * ) Notice: Subject to any disclaimer, the term of this patent is extended or adjusted under 35 U.S.C. 154(b) by 20 days.

(21) Appl. No.: 11/791,882

(22) PCT Filed: Dec. 5, 2005

(86) PCT No.: PCT/EP2005/056477

§ 371 (c)(1),
(2), (4) Date: Jul. 5, 2007

(87) PCT Pub. No.: WO2006/061366

PCT Pub. Date: Jun. 15, 2006

(65) Prior Publication Data

US 2008/0027126 A1    Jan. 31, 2008

Related U.S. Application Data

(60) Provisional application No. 60/633,612, filed on Dec. 6, 2004.

(51) Int. Cl.
*A61K 31/4015* (2006.01)
*C07D 207/12* (2006.01)
(52) U.S. Cl. .................. 514/424; 548/543; 548/556
(58) Field of Classification Search .............. 514/424; 548/543, 556
See application file for complete search history.

(56) References Cited

U.S. PATENT DOCUMENTS

| | | | |
|---|---|---|---|
| 3,873,566 A | 3/1975 | Scribner | |
| 4,003,911 A | 1/1977 | Scribner | |
| 4,033,989 A | 7/1977 | Bundy | |
| 4,090,019 A | 5/1978 | Williams et al. | |
| 4,138,407 A | 2/1979 | Cassidy et al. | |
| 4,156,730 A | 5/1979 | Moore et al. | |
| 4,211,876 A | 7/1980 | Scribner | |
| 4,262,008 A * | 4/1981 | Cassidy et al. | 514/421 |
| 4,299,970 A | 11/1981 | Cassidy et al. | |
| 5,606,814 A | 3/1997 | Szywalla et al. | |
| 5,759,789 A | 6/1998 | Abramovitz et al. | |
| 6,211,197 B1 | 4/2001 | Belley et al. | |
| 6,288,120 B1 | 9/2001 | Cameron et al. | |
| 6,395,499 B1 | 5/2002 | Abramovitz et al. | |

FOREIGN PATENT DOCUMENTS

| | | |
|---|---|---|
| EP | 0752421 A1 | 1/1997 |
| EP | 1110949 A1 | 6/2001 |
| WO | WO 96/03380 A1 | 2/1996 |
| WO | WO 96/06822 A1 | 3/1996 |
| WO | WO 97/00863 A1 | 1/1997 |
| WO | WO 97/00864 A1 | 1/1997 |
| WO | WO 99/02164 A1 | 1/1999 |
| WO | WO 02/24647 A1 | 3/2002 |
| WO | WO 03/007941 A1 | 1/2003 |
| WO | WO 03/009872   * | 2/2003 ............... 514/424 |
| WO | WO 03/009872 A1 | 2/2003 |

OTHER PUBLICATIONS

Partial STN search report with cited compound in WO 2003/009872.*
Barraclough, Paul et al, "Synthesis of Hexahydrocyclopentimidazol-2-(1*H*)-one Derivatives Displaying Selective DP-Receptor Agonist Properties," *Bioorganic & Medicinal Chemistry* 4(1): 81-90 (1996).
Abramovitz, M., et al., "The Utilization of Recombinant Prostanoid Receptors to Determine the Affinities and Selectivities of Prostaglandins and Related Analogs," *Biochimica et Biophysica Acta*, 1483: 285-293 (2000).
Bennett, G., et al., "Synthesis and Biological Activity of a Series of 1-Aryl-3-pyrazolidinones," *Journal of Medicinal Chemistry*, 19(5): 715-717 (1976).
Boie, Y., et al., "Molecular Cloning and Characterization of the Four Rat Prostaglandin E$_2$ Prostanoid Receptor Subtypes," *European Journal of Pharmacology*, 340: 227-241 (1997).
Boyce, S., et al., "Rapid Communication L-745,337: A Selective Inhibitor of Cyclooxygenase-2 Elicits Antinociception But Not Gastric Ulceration in Rats," *Neuropharmacology*, 33(12): 1609-1611 (1994).
Chan, C., et al., "A Selective Inhibitor of Cyclooxygenase-2 Reverses Endotoxin-induced Pyretic Responses in Non-human Primates," *European Journal of Pharmacology*, 327: 221-225 (1997).
Chan, C., et al., "Pharmacology of a Selective Cyclooxygenase-2 Inhibitor, L-745,337: A Novel Nonsteroidal Anti-inflammatory Agent With an Ulcerogenic Sparing Effect in Rat and Nonhuman Primate Stomach," *The Journal of Pharmacology and Experimental Therapeutics*, 274(3): 1531-1537 (1995).
Coleman, R., et al., "VIII. International Union of Pharmacology: Classification of Prostanoid Receptors: Properties, Distribution, and Structure of the Receptors and Their Subtypes," *Pharmacological Reviews*, 46(2): 205-229 (1994).
Coleman, R., et al., "Prostanoids and Their Receptors," In 3 *Comprehensive Medicinal Chemistry*, (Hansch, C., et al., eds. (UK: Pergamon Press)), pp. 643-714 (1990).
Fleisch, J., et al., "LY171883, 1-<2-Hydroxy-3-Propyl-4-<4-(1H-Tetrazol-5-yl) Butoxy>Phenyl>Ethanone, an Orally Active Leukotriene D$_4$ Antagonist," *The Journal of Pharmacology and Experimental Therapeutics*, 233(1): 148-157 (1985).
"Eicosanoids From Biotechnology to Therapeutic Applications," Folco, G., et al., eds., (NY: Plenum Press), (1996).

(Continued)

*Primary Examiner*—Yong Chu
(74) *Attorney, Agent, or Firm*—Joachim Seemann; EMD Serono, Inc.

(57) ABSTRACT

The present invention is directed to compounds that may be used as agonists of prostaglandin receptors. More specifically, the specification describes methods and compositions for making and using DP1 receptor agonists that are pyrrolidin-2-one derivatives.

30 Claims, No Drawings

OTHER PUBLICATIONS

Formica, C., et al., "Comparative Assessment of Bone Mineral Measurements Using Dual X-ray Absorptiometry and Peripheral Quantitative Computed Tomography," *Osteoporosis International*, 8(5): 460-467 (1998).

Gardiner, P., "Characterization of Prostanoid Relaxant/Inhibitory Receptors (φ) Using a Highly Selective Agonist, TR4979," *British Journal of Pharmacology*, 87(1): 45-56 (1986).

Hammad, H., et al., "Prostaglandin $D_2$ Inhibits Airway Dendritic Cell Migration and Function in Steady State Conditions by Selective Activation of the D Prostanoid Receptor 1," *The Journal of Immunology*, 171(8): 3936-3940 (2003).

Hawcroft, G., et al., "Expression of Prostaglandin $D_2$ Receptors DP1 and DP2 by Human Colorectal Cancer Cells," *Cancer Letters*, 210: 81-84 (2004).

Ichikawa, A., et al., "Molecular Aspects of the Structures and Functions of the Prostaglandin E Receptors," *Journal of Lipid Mediators and Cell Signaling*, 14: 83-87 (1996).

Minami, T., et al., "Characterization of EP-receptor Subtypes Involved in Allodynia and Hyperalgesia Induced by Intrathecal Administration of Prostaglandin $E_2$ to Mice," *British Journal of Pharmacology*, 112(3): 735-740 (1994).

Monneret, G., et al., "Prostaglandin $D_2$ is a Potent Chemoattractant for Human Eosinophils That Acts Via a Novel DP Receptor," *Blood*, 98(6): 1942-1948 (2001).

Narumiya, S., et al., "Prostanoid Receptors: Structures, Properties, and Functions," *Physiological Reviews*, 79(4): 1193-1226 (1999).

Takayama, K., et al., "Prostaglandin $E_2$ Suppresses Chemokine Production in Human Macrophages Through the EP4 Receptor," *The Journal of Biological Chemistry*, 277(46): 44147-44154 (2002).

Thivierge, M., et al., "Prostaglandin $E_2$ Induces Resistance to Human Immunodeficiency Virus-1 Infection in Monocyte-derived Macrophages: Downregulation of CCR5 Expression by Cyclic Adenosine Monophosphate," *Blood*, 92(1): 40-45 (1998).

Tsugeno, H., et al., "Vertebral Fracture and Cortical Bone Changes in Corticosteroid-induced Osteoporosis," *Osteoporosis International*, 13(8): 650-656 (2002).

Ushikubi, F., et al., "Roles of Prostanoids Revealed From Studies Using Mice Lacking Specific Prostanoid Receptors," *Japan Journal of Pharmacology*, 83: 279-285 (2000).

WHO Technical Report Series: 843, "Assessment of Fracture Risk and Its Application to Screening for Postmenopausal Osteoporosis," *WHO Study Group*, (Switzerland: World Health Organization) (1994).

\* cited by examiner

PYRROLIDIN-2-ONE DERIVATIVES FOR USE AS DP₁ RECEPTOR AGONISTS

RELATED APPLICATIONS

This application is the U.S. National Stage of International Application No. PCT/EP2005/056477, filed Dec. 5, 2005, published in English, and claims priority under 35 U.S.C. § 119 or 365 to U.S. Provisional Application No. 60/633,612, filed Dec. 6, 2004.

BACKGROUND

1. Field of the Invention

The present invention is generally directed to pyrrolidin-2-one derivatives and methods and compositions that employ such compounds. In particular embodiments, the compounds are useful as agonists of the $DP_1$ receptor.

2. Background of the Related Art

Prostaglandins (PGs), members of the prostanoid family, are formed by the actions of cyclooxygenases 1 and 2 on arachidonic acid. The biological activities of PGs include, for example, contraction and relaxation of smooth muscle, inhibition and enhancement of neurotransmitter release, inhibition of lipolysis, inhibition of gastric secretion, inhibition of inflammatory mediator release (Coleman et al., Prostanoids and Their Receptors. In Comprehensive Medicinal Chemistry, vol. 3 Ed. J. C. Emmett, 643-714, Pergammon Press, Oxford, UK, 1990) that are mediated by different receptor subtypes. To date, there are at least 8 known receptors that mediate the action of PGs. PGE2 has 4 receptor subtypes ($EP_{1-4}$ receptors), whereas PGs $D_2$, $F_2$, $I_2$, and thromboxane (TX) A2 each have a single receptor (DP, FP, IP, and TP receptors, respectively; Narumiya et al., *Physiol Rev.* 79:1193-1226 1999). Further descriptions of these receptors may be found in e.g., U.S. Pat. Nos. 5,606,814 and 5,759,789.

Studies from knock-out mice lacking each type and subtype of the EP receptor are instructive with respect to the roles of different prostaglandin receptors. For example mice lacking EP receptors showed different roles for the various different types and subtypes of EP receptors (Ushikubi at al. Jpn. J. Pharmacol., 83, 279-285, 2000) in various mechanisms such as ovulation, blood pressure control, closure of ductus arteriosus and bone resorption. Additional roles of EP receptors have been reported such as smooth muscle relaxation in cat trachea for $EP_2$, vasodilatation for $EP_4$ (Gardinier, Br. J. Pharmac. 1986, 87, 45-56; Coleman et al. 1994 Pharmacological Reviews 46 (2), 205-229) and anti-inflammatory activity for $EP_4$ (Takayama et al., The Journal of Biological Chemistry, 277, 46, 44147-44154, 2002). Renal Prostaglandin E2 (PGE2) is crucial for normal renal function by dilating the glomerular microcirculation and vasa recta, supplying the renal medulla and modulating salt and water transport in the distal tubule. There are multiple (at least two) receptor types for DP. Studies similar to the EP receptor studies would be instructive on the roles of the different DP receptors.

Prostaglandin E2 (PGE2) is a natural ligand for all subtypes of the EP receptor. Consequently, selective effects on one of the sub-types of the EP receptor is difficult to achieve with the endogenous prostaglandins.

Certain prostanoid receptors and modulators of those receptors have been largely reported (Eicosanoids: From Biotechnology to Therapeutic Applications (Plenum Press, New York); Journal of Lipid Mediators and Cell Signalling 14: 83-87 (1996); The British Journal of Pharmacology, 112: 735-740 (1994); WO 96/06822; WO 97/00863; WO 97/00864; WO 96/03380; EP 752421; U.S. Pat. Nos. 6,211,197, 4,211,876; 3,873,566; and Bennett et al. J. Med. Chem., 19 (5): 715-717 (1976).

Certain prostaglandin ligands and analogs have been reported to provide biological activity associated with prostaglandins (U.S. Pat. Nos. 6,288,120; 6,211,197; 4,090,019; 4,033,989; 4,003,911). E-type prostaglandin effects have been reported to be mediated through interaction with the prostaglandin E receptor(s). Certain compounds also have been reported as $EP_4$ agonists (WO 02/24647, EP1110949A1, W003/009872 and WO 03/007941).

It would be desirable to have new compounds and methods for treatment of diseases and disorders associated with the prostaglandin family of compounds.

SUMMARY OF THE INVENTION

The present invention is directed to compounds that may be used as agonists of prostaglandin receptors. More specifically, the specification describes methods and compositions for making and using $DP_1$ receptor agonists that are pyrrolidin-2-one derivatives. Exemplary such compounds have the formula I:

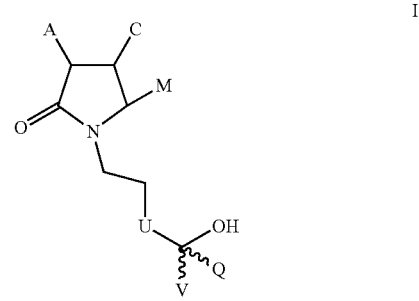

wherein

A and C are each independently hydrogen or hydroxy;

M is selected from the group consisting of optionally substituted $C_1$-$C_7$ alkyl, $C_1$-$C_6$ alkenyl, $C_1$-$C_6$ alkynyl and —$(CH_2)_q$-B wherein B is selected from the group comprising optionally substituted carbocyclic aryl, optionally substituted heteroalicyclic having from 3 to 8 ring atoms and at least one N, O or S ring atom and a heteroaromatic group having a single ring with 5 or 6 ring atoms and at least one N, O or S ring atom; wherein q in "—$(CH_2)_q$-B" is selected from 1, 2, 3 and 4;

U is $(CH_2)_p$ wherein p is selected from 0, 1 and 2;

V and Q are each independently hydrogen, optionally substituted alkyl, optionally substituted alkenyl, optionally substituted alkynyl, $C_1$-$C_6$ heteroalkyl, $C_3$-$C_6$ cycloalkyl, $C_1$-$C_6$ alkyl, $C_3$-$C_6$ heterocycloalkyl $C_1$-$C_6$ alkyl, arylalkyl, —$CR^1R^2$-W, wherein $R^1$ and $R^2$ are independently selected from H and $C_1$-$C_6$ alkyl; or $R^1$ and $R^2$ can form an $C_3$-$C_6$ cycloalkyl with the carbon they are attached to;

W is selected from hydrogen, $C_1$-$C_6$ alkyl, $C_3$-$C_6$ cycloalkyl, $C_3$-$C_6$ cycloalkyl $C_1$-$C_6$ alkyl, aryl and heteroaryl; with at least one of V and Q being other than hydrogen; and pharmaceutically acceptable salts thereof. In particularly preferred compounds, A and C are each hydrogen. In specific compounds of the invention, B is optionally substituted carbocyclic aryl, or an optionally substituted phenyl.

In more particular embodiments, the compounds may have the formula II or Formula:

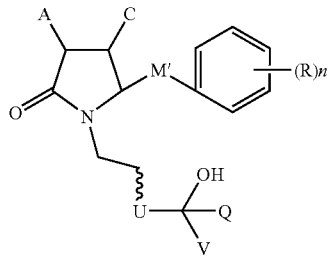

II wherein M' is selected from the group consisting optionally substituted $C_1$-$C_7$ alkyl, $C_1$-$C_6$ alkenyl, and $C_1$-$C_6$ alkynyl;

R is C(=O)Z where Z is selected from hydrogen, hydroxy, optionally substituted alkoxy and optionally substituted alkyl; or R is amino or optionally substituted alkylamine; In specific embodiments, n is 1 or 2

U is $(CH_2)p$ wherein p is selected from 0, 1 and 2;

V and Q are each independently selected from hydrogen, optionally substituted alkyl, optionally substituted alkenyl, optionally substituted alkynyl, $C_1$-$C_6$ heteroalkyl, $C_3$-$C_6$ cycloalkyl $C_1$-$C_6$ alkyl, $C_3$-$C_6$ heterocycloalkyl $C_1$-$C_6$ alkyl, arylalkyl and —$CR^1R^2$-W, wherein $R^1$ and $R^2$ are independently selected from H and $C_1$-$C_6$ alkyl; or $R^1$ and $R^2$ can form an $C_3$-$C_6$ cycloalkyl with the carbon they are attached to;

W is selected from hydrogen, $C_1$-$C_6$ alkyl, $C_3$-$C_6$ cycloalkyl, $C_3$-$C_6$ cycloalkyl $C_1$-$C_6$ alkyl, aryl and heteroaryl; with at least one of V and Q being other than hydrogen; and pharmaceutically acceptable salts thereof.

Also encompassed by the formula I are preferred exemplary compounds having the formula III:

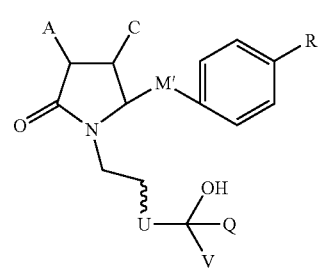

III in which M' is selected from the group consisting optionally substituted $C_1$-$C_7$ alkyl, $C_1$-$C_6$ alkenyl, and $C_1$-$C_6$ alkynyl;

R is C(=O)Z where Z is selected from hydrogen, hydroxy, optionally substituted alkoxy and optionally substituted alkyl; or R is amino or optionally substituted alkylamine;

U is $(CH_2)p$ wherein p is selected from 0, 1 and 2; V and Q are each independently selected from hydrogen, optionally substituted alkyl, optionally substituted alkenyl, optionally substituted alkynyl, $C_1$-$C_6$ heteroalkyl, $C_3$-$C_6$ cycloalkyl $C_1$-$C_6$ alkyl, $C_3$-$C_6$ heterocycloalkyl $C_1$-$C_6$ alkyl, arylalkyl and —$CR^1R^2$-W, wherein $R^1$ and $R^2$ are independently selected from H and $C_1$-$C_6$ alkyl; or $R^1$ and $R^2$ can form an $C_3$-$C_6$ cycloalkyl with the carbon they are attached to;

W is selected from hydrogen, $C_1$-$C_6$ alkyl, $C_3$-$C_6$ cycloalkyl, $C_3$-$C_6$ cycloalkyl $C_1$-$C_6$ alkyl, aryl and heteroaryl; with at least one of V and Q being other than hydrogen; and pharmaceutically acceptable salts thereof.

Other preferred compounds encompassed by the formula I include preferred compounds of the formula IV:

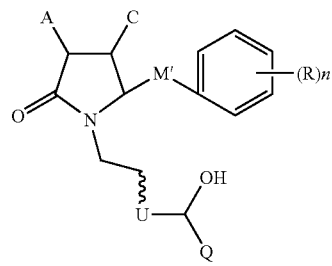

IV in which M' is selected from the group consisting optionally substituted $C_1$-$C_7$ alkyl, $C_1$-$C_6$ alkenyl, and $C_1$-$C_6$ alkynyl;

R is C(=O)Z where Z is selected from hydrogen, hydroxy, optionally substituted alkoxy and optionally substituted alkyl; or R is amino or optionally substituted alkylamine; n is an integer selected from 0, 1, 2, 3, 4 and 5;

U is $(CH_2)$ p wherein p is selected from 0, 1 and 2;

Q is optionally substituted from alkyl, preferably having 1 to about 12 carbon atoms, optionally substituted alkenyl preferably having 2 to about 12 carbon atoms, optionally substituted alkynyl preferably having from 2 to about 12 carbon atoms, $C_1$-$C_6$ heteroalkyl, $C_3$-$C_6$ cycloalkyl $C_1$-$C_6$ alkyl, $C_3$-$C_6$ heterocycloalkyl $C_1$-$C_6$ alkyl, aryl $C_1$-$C_6$ alkyl and —$CR^1R^2$-W, wherein $R^1$ and $R^2$ are independently selected from H and $C_1$-$C_6$ alkyl; or $R^1$ and $R^2$ can form a $C_3$-$C_6$ cycloalkyl with the carbon they are attached to;

W is selected from hydrogen, $C_1$-$C_6$ alkyl, $C_3$-$C_6$ cycloalkyl, $C_3$-$C_6$ cycloalkyl $C_1$-$C_6$ alkyl, aryl, heteroaryl and aryl $C_1$-$C_6$ alkyl; and pharmaceutically acceptable salts thereof.

In specific preferred compounds of the invention, in compounds of any of formulae I to IV, p is zero.

Other preferred compounds encompassed by the formula I include the preferred compounds having formula V:

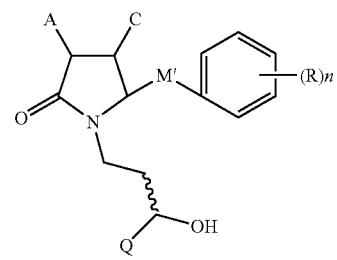

V in which M' is selected from the group consisting optionally substituted $C_1$-$C_7$ alkyl, $C_1$-$C_6$ alkenyl, and $C_1$-$C_6$ alkynyl;

R is C(=O)Z where Z is selected from hydrogen, hydroxy, optionally substituted alkoxy and optionally substituted alkyl; or R is amino or optionally substituted alkylamine; n is an integer selected from 0, 1, 2, 3, 4 and 5;

Q is selected from optionally substituted alkyl, optionally substituted alkenyl, optionally substituted alkynyl, or optionally substituted arylalkyl, $C_1$-$C_6$ heteroalkyl, $C_3$-$C_6$ cycloalkyl $C_1$-$C_6$ alkyl, $C_3$-$C_6$ heterocycloalkyl $C_1$-$C_6$ alkyl, aryl $C_1$-$C_6$ alkyl and —$CR^1R^2$-W, wherein $R^1$ and $R^2$ are independently selected from H and $C_1$-$C_6$ alkyl; or $R^1$ and $R^2$ can form an $C_3$-$C_6$ cycloalkyl with the carbon they are attached to;

W is selected from hydrogen, $C_1$-$C_6$ alkyl, $C_3$-$C_6$ cycloalkyl, $C_3$-$C_6$ cycloalkyl $C_1$-$C_6$ alkyl, aryl, heteroaryl and aryl $C_1$-$C_6$ alkyl; and pharmaceutically acceptable salts thereof. In compounds of formula V, n is preferably 1 and R is preferably a para-substituent. In more particular embodiments, R is —C(O)OH. In other preferred embodiments, in the compound of formula V, Q is specifically defined as a straight or branched $C_1$-$C_{12}$ alkyl or optionally substituted arylalkyl.

In preferred compounds of formula V, R is —C(O)OH is in a "para" position and n is 1; Q is $CR^1R^2$-W, wherein $R^1$ and $R^2$ are independently selected from H and $C_1$-$C_6$ alkyl; or $R^1$ and $R^2$ can form an $C_3$-$C_6$ cycloalkyl with the carbon they are attached to; W is selected from hydrogen, $C_1$-$C_6$ alkyl, $C_2$-$C_6$ alkenyl, $C_3$-$C_6$ cycloalkyl, $C_3$-$C_6$ cycloalkyl $C_1$-$C_6$ alkyl, aryl, heteroaryl and aryl $C_1$-$C_6$ alkyl; and pharmaceutically acceptable salts thereof.

Other exemplary embodiments encompass compounds of formula V in which R is —C(O)OH present at the "para" position; n is 1; Q is $CR^1R^2$-W, wherein $R^1$ and $R^2$ are independently selected from H and $C_1$-$C_6$ alkyl; or $R^1$ and $R^2$ can form a $C_3$-$C_6$ cycloalkyl with the carbon they are attached to; W is selected from hydrogen, $C_1$-$C_6$ alkyl, $C_3$-$C_6$ cycloalkyl $C_1$-$C_6$ alkyl, and aryl; and pharmaceutically acceptable salts thereof.

In specific embodiments, the compound of formula I is one in which M has a formula:

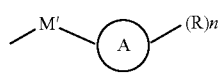

wherein M' is selected from the group consisting optionally substituted $C_1$-$C_7$ alkyl, $C_1$-$C_6$ alkenyl, and $C_1$-$C_6$ alkynyl;

A is selected from the group consisting of optionally substituted optionally substituted pyridyl, pyrrolyl, furyl (furanyl), thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl and benzoquinolyl; and R is C(=O)Z where Z is selected from hydrogen, hydroxy, optionally substituted alkoxy and optionally substituted alkyl; or R is amino or optionally substituted alkylamine; n is an integer selected from 0, 1, 2, 3, 4 and 5.

In other embodiments, M is selected from the group consisting of:

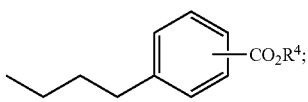

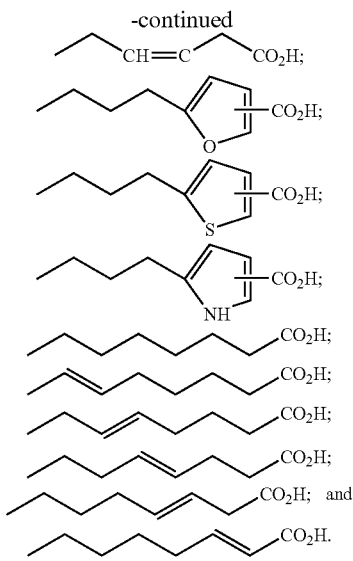

M also may be selected from the group consisting of

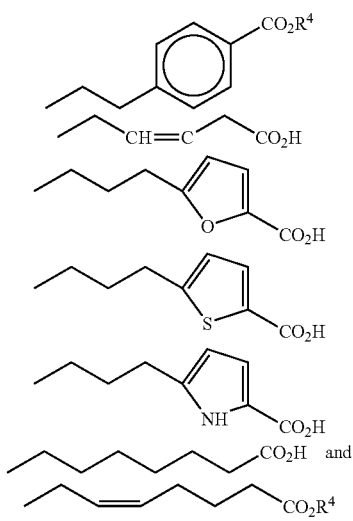

wherein $R^4$ is selected from the group consisting of H, an alkyl group an aryl group or a salt.

In specific preferred embodiments, M is

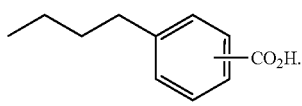

In other preferred embodiments, M is

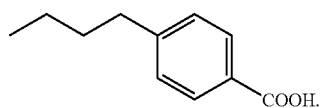

In other preferred embodiments, M is

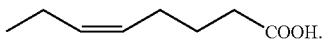

Additional compounds of the invention are encompassed by formulae I.2, I.2.1, II.2, III.2, IV.2, and V.2 as presented in the following formulae. The substituents A, B, C, R, U, Q, V, and the integer n are as defined above.

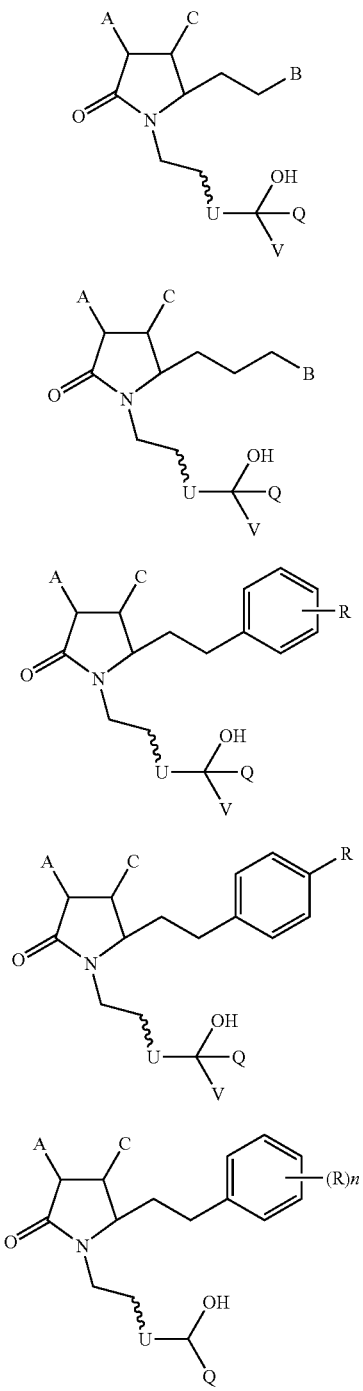

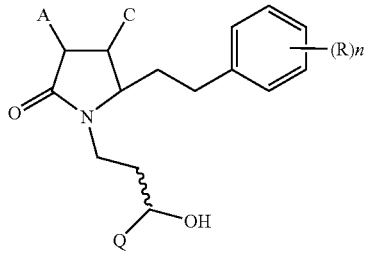

In addition to the specific compounds described in detail herein, the present invention is further directed to any of said compounds for use as a medicament. In other embodiments, the compounds described herein are contemplated for use in the manufacture of a medicament for the treatment of a disease or disorder associated with prostaglandin deficiency.

The invention is further directed to methods of treating a disease or disorder in a mammal comprising augmenting or increasing the action of a prostaglandin receptor by administering to the mammal an effective amount of a compound of the present invention. The disease may be any disease which is mediated through the action of prostaglandins. In particular, non-limiting examples, the mammal is suffering from or is susceptible to ichthyosis, dry eye, a sleep disorder, gastric ulcers, undesired muscle contraction, inflammatory disorders, erectile dysfunction, asthma, hypertension, undesired blood clotting, infertility or a fertility disorder, eosinophil disorder, sexual dysfunction, glaucoma, elevated intraocular pressure, renal dysfunction, an immune deficiency disease or disorder, AIDS, and undesired bone loss. The mammal may be a domestic animals, companion animals, zoo animals or a laboratory animal. In specific embodiments, the mammal is selected from the group consisting of cows, sheep, pigs, horses and goats, companion animals such as dogs and cats, exotic and/or zoo animals, laboratory animals including mice rats, rabbits, guinea pigs and hamsters. In preferred embodiments, the mammal is a human. The mammal may be a male or a female. In embodiments, in which the mammal is a female, the female may be one suffering from or susceptible to, preterm labor, dysmenorrhea, preeclampsia or eclampsia. In other embodiments the female in need of treatment is in late stage pregnancy and in need of control of cervical ripening. In other embodiments, she is suffering from or susceptible to infertility. In still other embodiments, the methods of the invention are useful in the treatment of a female suffering from an ovulatory disorder.

Thus, the methods of the invention are in certain embodiments directed to a treating a mammal suffering from or susceptible to preterm labor, dysmenorrhea, asthma, hypertension, a fertility disorder, undesired blood clotting, preeclampsia, eclampsia, an eosinophil disorder, undesired bone loss, sexual dysfunction, renal dysfunction, an immune deficiency disorder, dry eye, ichthyosis, elevated intraocular pressure, a sleep disorder, a gastric ulcer, or an inflammatory disorder, comprising administering to the mammal an effective amount of a compound of the invention, such as the compounds described herein by any of formulae I to V.

Use of the compounds of the invention for the preparation of a medicament to treat a disease or disorder associated with prostaglandin is particularly contemplated.

Further, the invention is directed to use of compounds described herein for the manufacture of a medicament to treat preterm labor, dysmenorrhea, asthma, hypertension, a fertility disorder, undesired blood clotting, preeclampsia, eclampsia, an eosinophil disorder, undesired bone loss, sexual dysfunction, renal dysfunction, an immune deficiency disorder, dry eye, ichthyosis, elevated intraocular pressure, a sleep disorder, a gastric ulcer or an inflammatory disorder.

The present invention is further directed to pharmaceutical compositions comprising a pharmaceutically acceptable carrier and one or more of the pyrrolidin-2-one derivatives described herein. In more particular embodiments, the compound in the pharmaceutical composition is packaged together with instructions for use of the compound to treat preterm labor, dysmenorrhea, asthma, hypertension, infertility or a fertility disorder, sexual dysfunction, undesired blood clotting, a destructive bone disease or disorder, preeclampsia or eclampsia, an eosinophil disorder, renal dysfunction, an immune deficiency disorder, dry eye, ichthyosis, elevated intraocular pressure, sleep disorder, or gastric ulcer.

Also described herein are methods of treating a fertility condition in a female, comprising the administration to said female a prostaglandin $DP_1$ receptor agonist, a pro-drug thereof or a pharmaceutical acceptable salt of said compound, pro-drug or a diastereoisomeric mixture of said compound, salt or pro-drug. In specific embodiments, the condition is infertility. In other more particular embodiments, the condition is an ovulatory disorder. In still further embodiments, the female is undergoing an ovulation induction or ART treatments. In particularly preferred therapeutic methods of the invention, the prostaglandin $DP_1$ receptor agonist is selected among compounds of formula VI:

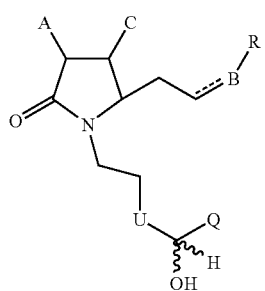

VI wherein each of A and C are independently H or OH, preferably H;

B is selected from the group consisting of optionally substituted $C_1$-$C_6$ alkyl, optionally substituted aryl $C_1$-$C_6$ alkyl, optionally substituted aryl $C_1$-$C_6$ heteroalkyl, optionally substituted heteroaryl $C_1$-$C_6$ alkoxy, optionally substituted aryl, optionally substituted heteroaryl, optionally substituted $C_3$-$C_6$ cycloalkyl and optionally substituted $C_3$-$C_6$ heterocycloalkyl, provided that when B is optionally substituted aryl, optionally substituted heteroaryl, optionally substituted $C_3$-$C_6$ cycloalkyl and optionally substituted $C_3$-$C_6$ heterocycloalkyl, the undefined bond linking B is a single bond;

The dotted line indicates an optional double bond;

R is C(=O) Z where Z is selected from hydrogen, hydroxy, optionally substituted alkoxy and optionally substituted alkyl; or R is amino or optionally substituted alkylamine; n is an integer selected from 0, 1, 2, 3, 4 and 5;

U is ($CH_2$) p wherein p is selected from 0, 1 and 2;

Q is optionally substituted from alkyl, preferably having 1 to about 12 carbon atoms, optionally substituted alkenyl preferably having 2 to about 12 carbon atoms, optionally substituted alkynyl preferably having from 2 to about 12 carbon atoms, $C_1$-$C_6$ heteroalkyl, $C_3$-$C_6$ cycloalkyl $C_1$-$C_6$ alkyl, $C_3$-$C_6$ heterocycloalkyl $C_1$-$C_6$ alkyl, aryl $C_1$-$C_6$ alkyl and —$CR^1R^2$-W, wherein $R^1$ and $R^2$ are independently selected from H and $C_1$-$C_6$ alkyl; or $R^1$ and $R^2$ can form a $C_3$-$C_6$ cycloalkyl with the carbon they are attached to;

W is selected from hydrogen, $C_1$-$C_6$ alkyl, $C_3$-$C_6$ cycloalkyl, $C_3$-$C_6$ cycloalkyl $C_1$-$C_6$ alkyl, aryl, heteroaryl and aryl $C_1$-$C_6$ alkyl; and pharmaceutically acceptable salts thereof.

More particularly, the prostaglandin $DP_1$ receptor agonist is selected among compounds of formula VI, wherein A is H; B is $C_1$-$C_6$ alkyl whereby B is linked by a single bond; R is C(=O)Z wherein Z is selected from hydrogen, hydroxy, alkoxy such as —O-alkyl and alkyl; or Z is selected from amino or alkylamine such as —$NR^1R^2$ where $R^1$ and $R^2$ are independently hydrogen or alkyl, —$NHSO_2R^3$ and —NHC(O)$R^3$ wherein $R^3$ is selected among $C_1$-$C_6$ alkyl and aryl; U is ($CH_2$)p wherein p is 0; Q is —$CR^4R^5$-W, wherein $R^4$ and $R^5$ are independently selected from H, halogen and $C_1$-$C_6$ alkyl; W is selected from $C_3$-$C_6$ cycloalkyl, $C_3$-$C_6$ heterocycloalkyl, optionally substituted aryl and heteroaryl; and pharmaceutically acceptable salts thereof.

In still other embodiments, the prostaglandin $DP_1$ receptor agonist is selected among compounds of formula VI, wherein A is H; B is $C_1$-$C_6$ alkyl; R is C(=O)Z wherein Z is selected from hydrogen, hydroxy, alkoxy; or R is heteroaryl; U is ($CH_2$)p wherein p is 0; Q is —$CH_2$-W, wherein W is selected from $C_3$-$C_6$ cycloalkyl, $C_3$-$C_6$ heterocycloalkyl, aryl and heteroaryl; and pharmaceutically acceptable salts thereof.

In still further embodiments, the prostaglandin $DP_1$ receptor agonist is selected among compounds of formula VI, wherein A is H; B is selected from aryl $C_1$-$C_6$ alkoxy, —$CH_2$-aryl and —$CH_2$-heteroaryl whereby B is linked by a single bond; R is C(=O) Z wherein Z is selected hydrogen, hydroxy and alkoxy; or R is heteroaryl; U is ($CH_2$)p wherein p is 0; Q is —$CH_2$-W, wherein W is selected from $C_3$-$C_6$ cycloalkyl, $C_3$-$C_6$ heterocycloalkyl, aryl and heteroaryl; and pharmaceutically acceptable salts thereof.

In yet additional embodiments, the prostaglandin $DP_1$ receptor agonist is selected among compounds of formula VI wherein A is H; B is substituted aryl whereby B is linked by a single bond; R is C(=O)Z wherein Z is hydroxy; U is ($CH_2$)p wherein p is 0; Q is —$CR^4R^5$-W, wherein $R^4$ and $R^5$ are independently selected from H and $C_1$-$C_6$ alkyl; or $R^4$ and $R^5$ can form a $C^3$-$C^6$ cycloalkyl with the carbon they are attached to; W is selected from $C_1$-$C_6$ alkyl, $C_3$-$C_6$ cycloalkyl $C_1$-$C_6$ alkyl, $C_3$-$C_6$ cycloalkyl, aryl and substituted phenyl; and pharmaceutically acceptable salts thereof.

In particularly preferred embodiments, prostaglandin $DP_1$ receptor agonist is selected from the group consisting of:

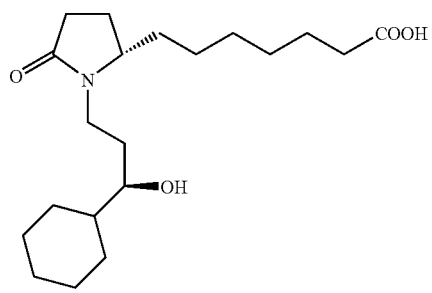

-continued
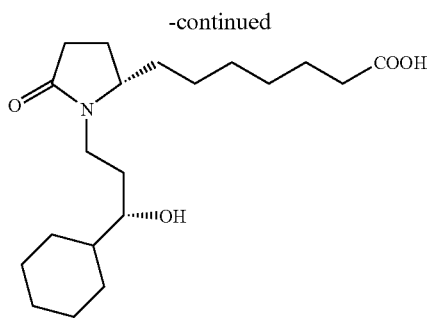
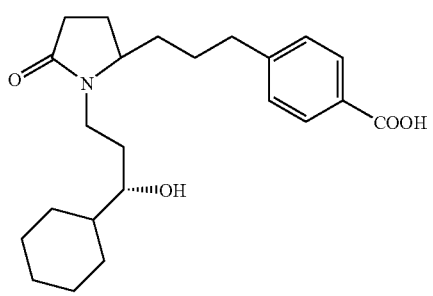
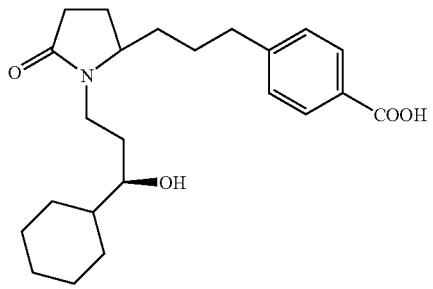
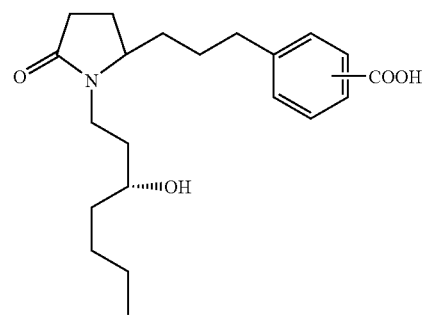
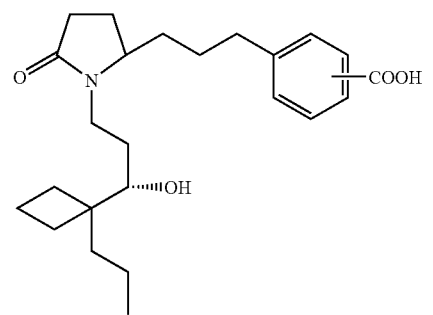
-continued
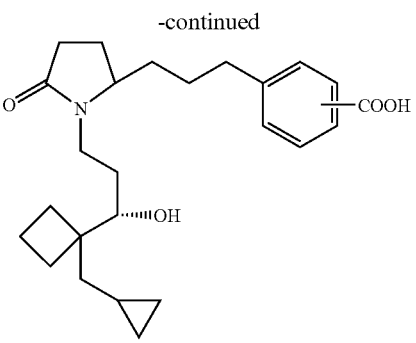
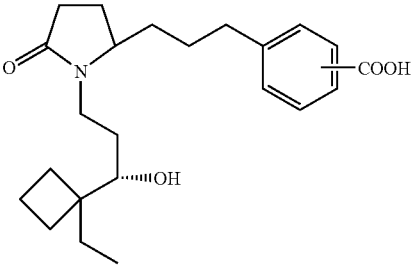
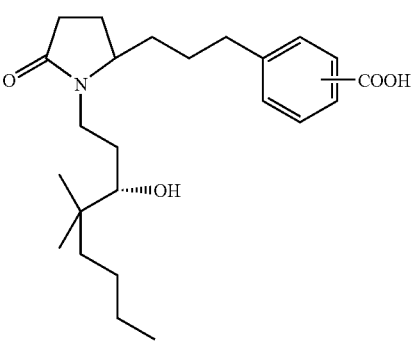
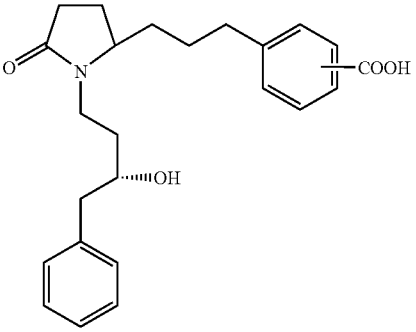
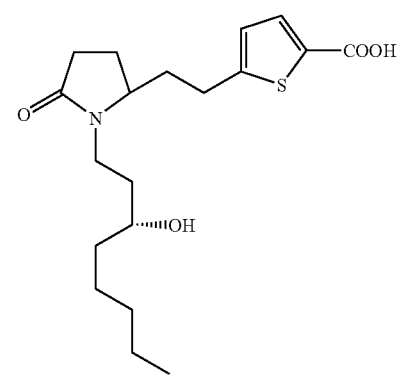

-continued
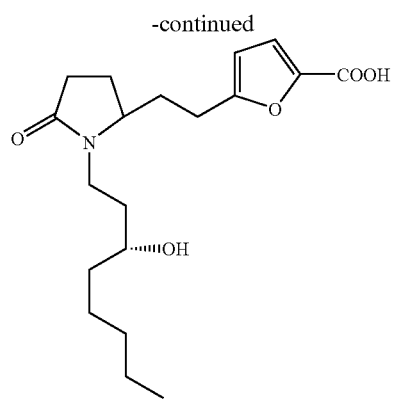
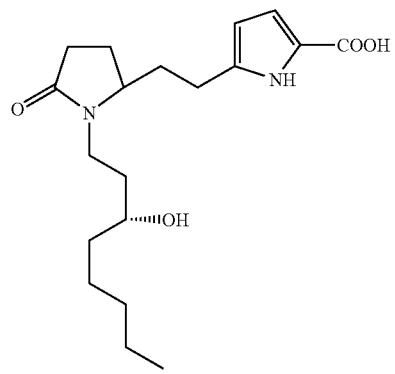
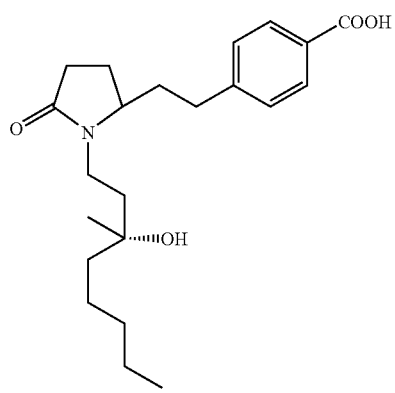
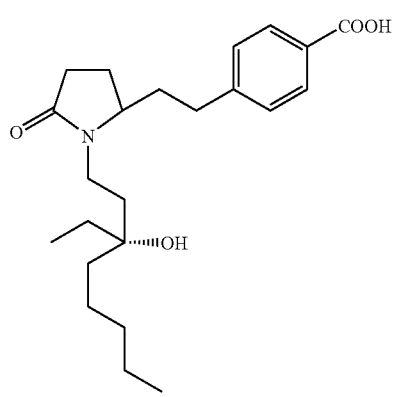
-continued
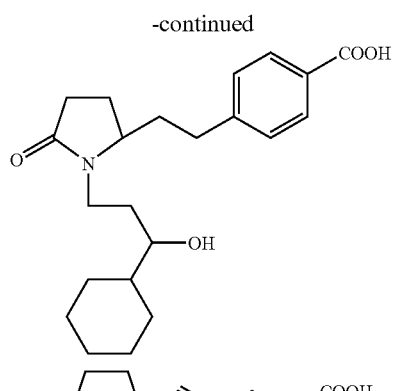
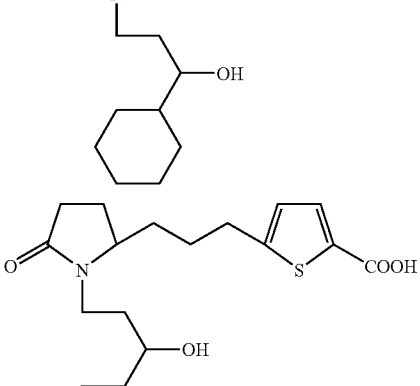
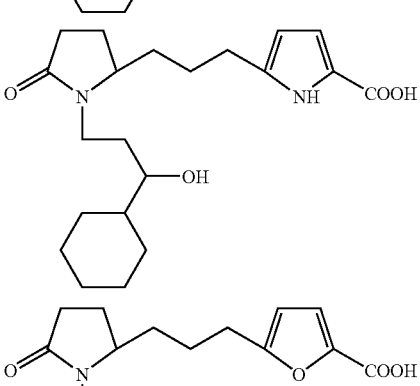
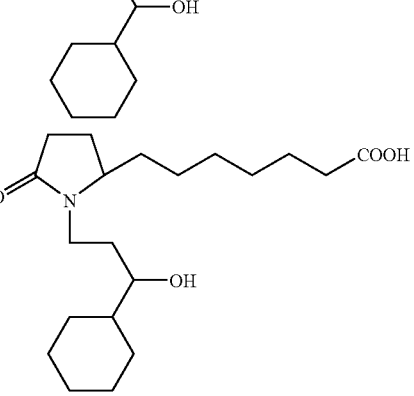

-continued

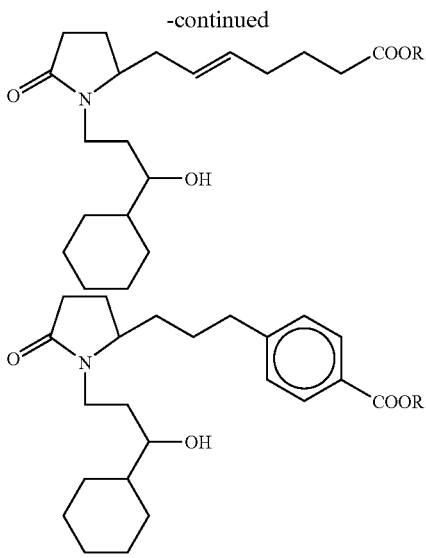

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

DESCRIPTION OF THE PREFERRED EMBODIMENTS

In the present application there are described a number of pyrrolidin-2-one derivatives that are useful for a variety of disorders, and in particular will be useful in the treatment of diseases or disorders associated with prostaglandins, such as inhibiting prostanoid induced smooth muscle contraction. Certain compounds of the invention generally having the structure depicted in Formula I:

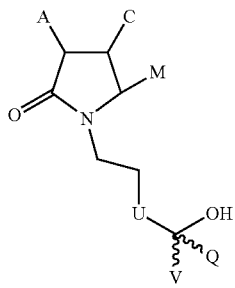

I wherein A and C are each independently hydrogen or hydroxy;

M is selected from the group consisting of optionally substituted $C_1$-$C_7$ alkyl, $C_1$-$C_6$ alkenyl, $C_1$-$C_6$ alkynyl and —($CH_2$)q-B wherein B is selected from the group comprising optionally substituted carbocyclic aryl, optionally substituted heteroalicyclic having from 3 to 8 ring atoms and at least one N, O or S ring atom and a heteroaromatic group having a single ring with 5 or 6 ring atoms and at least one N, O or S ring atom; wherein q in "—($CH_2$)q-B" is selected from 1, 2, 3, and 4;

U is ($CH_2$)p wherein p is selected from 0, 1 and 2;

V and Q are each independently selected from the group comprising or consisting of hydrogen, optionally substituted alkyl preferably having 1 to about 12 carbon atoms, optionally substituted alkenyl preferably having 2 to about 12 carbon atoms, optionally substituted alkynyl preferably having from 2 to about 12 carbon atoms, optionally substituted $C_1$-$C_6$ heteroalkyl, optionally substituted $C_3$-$C_6$ cycloalkyl $C_1$-$C_6$ alkyl, optionally substituted $C_3$-$C_6$ heterocycloalkyl $C_1$-$C_6$ alkyl, optionally substituted aryl $C_1$-$C_6$ alkyl and —$CR^1R^2$-W, wherein $R^1$ and $R^2$ are independently selected from H and optionally substituted $C_1$-$C_6$ alkyl, preferably H; or $R^1$ and $R^2$ can form an optionally substituted $C_3$-$C_6$ cycloalkyl with the carbon they are attached to, preferably an optionally substituted $C_3$, $C_4$ or $C_5$ cycloalkyl;

W is selected from the group comprising or consisting of hydrogen, optionally substituted $C_1$-$C_6$ alkyl, optionally substituted $C_3$-$C_6$ cycloalkyl, optionally substituted $C_3$-$C_6$ cycloalkyl $C_1$-$C_6$ alkyl, optionally substituted aryl, optionally substituted heteroaryl and optionally substituted aryl $C_1$-$C_6$ alkyl; with at least one of V and Q being other than hydrogen; and pharmaceutically acceptable salts thereof.

In Formula I, preferably substituent B is a substituted carbocyclic aryl, heteroalicyclic, or heteroaromatic group, e.g. such a ring group substituted by a carboxylate (e.g., —COOR where R is hydrogen or $C_1$-$C_6$ alkyl), amide (e.g. —CONHR where R is H or $C_1$-$C_6$ alkyl), and the like.

Preferred compounds of Formula I include those compounds where substituent A is hydrogen and/or substituent B is an optionally substituted thiophene, optionally substituted pyrrole, optionally substituted furan or optionally substituted carbocyclic aryl group particularly optionally substituted phenyl, such as compounds of the following Formula II:

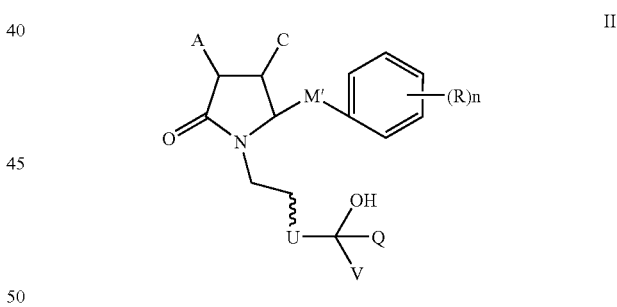

II wherein in Formula II, A, C, U, V and Q are the same as defined for formula I above;

M' is selected from the group consisting optionally substituted $C_1$-$C_7$ alkyl, $C_1$-$C_6$ alkenyl, and $C_1$-$C_6$ alkynyl;

R is C(=O)Z where Z is selected from the group comprising or consisting of hydrogen, hydroxy, alkoxy such as —O-alkyl preferably —O—$C_1$-$C_4$ alkyl (i.e., to provide $C_1$-$C_4$ ester, including methyl, ethyl, propyl or butyl esters) and optionally substituted alkyl preferably $C_1$-$C_6$ alkyl; or R is amino or alkylamine such as $NR^1R^2$ where $R^1$ and $R^2$ are independently hydrogen or optionally substituted alkyl preferably $C_1$-$C_6$ alkyl having 1 to 6; n is an integer selected from 0, 1, 2, 3, 4 (where available phenyl ring positions are all hydrogen-substituted) and 5, and preferably n is selected from 0, 1 and 2; and pharmaceutically acceptable salts thereof.

Preferred compounds of Formulae I and II above include those having a para-substituted phenyl moiety as a component of the substituent of the pyrrolidinone ring nitrogen, such as compounds of following Formula III:

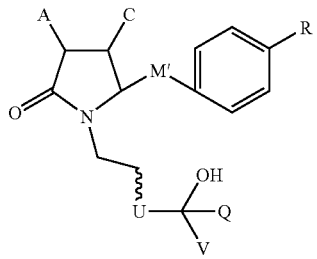

III wherein in Formula III A, C, U, Q and V are the same as defined for Formula I; M' and R are the same as defined for Formula II, and pharmaceutically acceptable salts thereof.

Also preferred are compounds of the above formulae wherein one of substituents Q and V is hydrogen and the other is a non-hydrogen group, such as compounds of the following Formula IV:

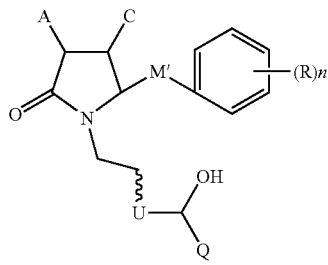

IV wherein in Formula IV:

U is the same as defined in Formula I;

M', R and n are the same as defined in Formula II; and

Q is selected from the group comprising or consisting of optionally substituted alkyl preferably having 1 to about 12 carbon atoms, optionally substituted alkenyl preferably having 2 to about 12 carbon atoms, optionally substituted alkynyl preferably having from 2 to about 12 carbon atoms, $C_1$-$C_6$ heteroalkyl, $C_3$-$C_6$ cycloalkyl $C_1$-$C_6$ alkyl, $C_3$-$C_6$ hetero heterocycloalkyl $C_1$-$C_6$ alkyl, optionally substituted aryl, alkyl and —$CR_1R_2$-W, wherein $R_1$ and $R_2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$, $C_4$ or $C_5$ cycloalkyl;

W is selected from the group comprising or consisting of hydrogen, optionally substituted $C_1$-$C_6$ alkyl, optionally substituted $C_3$-$C_6$ cycloalkyl, optionally substituted $C_3$-$C_6$ cycloalkyl $C_1$-$C_6$ alkyl, optionally substituted aryl, optionally substituted heteroaryl and optionally substituted arylalkyl; and pharmaceutically acceptable salts thereof.

Also preferred are compounds of the above formulae where U is absent (p=0), to thereby compounds of the following Formula V:

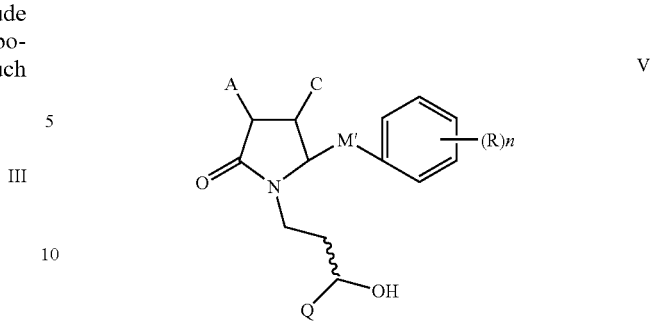

V wherein Formula V:

M', R and n are the same as defined in Formula II; and

Q is selected from the group consisting of optionally substituted (straight or branched) alkyl preferably having 1 to about 12 carbon atoms, more preferably from 1 to 9 carbon atoms (e.g., a pentyl, hexyl, heptyl or nonyl moiety), optionally substituted alkenyl preferably having 2 to about 12 carbon atoms, optionally substituted alkynyl preferably having from 2 to about 12 carbon atoms, $C_1$-$C_6$ heteroalkyl, $C_3$-$C_6$ cycloalkyl $C_1$-$C_6$ alkyl, $C_3$-$C_6$ heterocycloalkyl $C_1$-$C_6$ alkyl, optionally substituted arylalkyl, e.g., an optionally substituted benzyl or a phenethyl and —CR1R2-W, wherein $R^1$ and $R^2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$ or $C_4$ cycloalkyl;

W is selected from the group consisting of hydrogen, optionally substituted $C_1$-$C_6$ alkyl, optionally substituted $C_3$-$C_6$ cycloalkyl, optionally substituted $C_3$-$C_6$ cycloalkyl $C_1$-$C_6$ alkyl, optionally substituted aryl, optionally substituted heteroaryl and optionally substituted aryl $C_1$-$C_6$ alkyl; and pharmaceutically acceptable salts thereof.

A group of preferred compounds of the invention includes compounds of formula V wherein R is C(=O)OH and is a "para" substituent; n is 1; and pharmaceutically acceptable salts thereof.

Q is selected from the group comprising or consisting of optionally substituted $C_1$-$C_6$ alkyl, optionally substituted $C_2$-$C_6$ alkenyl and —$CR^1R^2$-W, wherein $R^1$ and $R^2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$ or $C_4$ cycloalkyl;

W is selected from the group comprising or consisting of hydrogen, optionally substituted $C_1$-$C_6$ alkyl, optionally substituted $C_3$-$C_6$ cycloalkyl, optionally substituted $C_3$-$C_6$ cycloalkyl, optionally substituted $C_3$-$C_6$ cycloalkyl $C_1$-$C_6$ alkyl, optionally substituted aryl and optionally substituted aryl $C_1$-$C_6$ alkyl; and pharmaceutically acceptable salts thereof.

Another more preferred group of compounds of the invention includes compounds of formula V, wherein R is C(=O)OH is in a "para" position whereby n is 1;

Q is —$CR^1R^2$-W, wherein $R^1$ and $R^2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$ or $C_4$ cycloalkyl;

W is selected from the group comprising or consisting of hydrogen, optionally substituted $C_1$-$C_6$ alkyl, optionally substituted $C_3$-$C_6$ cycloalkyl $C_1$-$C_6$ alkyl and optionally substituted aryl; and pharmaceutically acceptable salts thereof.

According to one embodiment, the compounds of the invention exhibit binding activity in a standard prostaglandin $DP_1$ receptor binding assay. Exemplary assay formats are set out in Example 5 below.

According to one embodiment, compounds of the present invention also can exhibit selective binding to the other prostaglandin receptors.

As discussed above, substituted 1,2-substituted 5-pyrrolidinone compounds of the invention are useful for treatment of diseases and disorders associated with the prostaglandin family of compounds. Therapeutic methods of the invention in general comprise administering an effective amount of one or more of the pyrrolidinone compounds as disclosed herein to a mammal in need thereof.

The pyrrolidinone compounds of the invention are particularly useful for treatment of a mammal suffering from or susceptible to (prophylactic therapy) pre-term labor, dysmenorrhea, asthma and other conditions treated by bronchodilation, inflammation, hypertension, undesired blood-clotting and other undesired platelet activities, pre-eclampsia and/or eclampsia, and eosinphil-related disorders. The pyrrolidinon-based compounds of the invention also are useful to treat a mammal suffering from or suspected of suffering from infertility, particularly a female suffering from infertility. The pyrrolidinone compounds of the invention may be particularly beneficial for treatment of female mammals suffering from an ovulatory disorder. Additionally, the compounds of the invention can be administered to females undergoing reproductive treatments such as in-vitro fertilization or implant procedures, e.g., to stimulate follicular development and maturation. The compounds of the invention also are useful to treat sexual dysfunction, including erectile dysfunction.

Preferred compounds of the invention also will be useful for treatment of undesired bone loss (e.g., osteoporosis, particularly in women) or otherwise promoting bone formation and treatment of other bone diseases such as Paget's disease, healing or replacement of bone grafts, and the like.

Compounds of the invention also are useful for treatment of a subject suffering from or susceptible to renal dysfunction, including a mammal suffering from or susceptible to acute or chronic renal failure.

Compounds of the invention also are useful for treatment of a subject suffering from or susceptible to an immune disorder including an immune deficiency disease or disorder, including such a disorder associated with a viral infection particularly a retroviral infection such as an HIV infection. Particularly benefited by such therapies will be a human suffering from or susceptible to AIDS (Thivierge et al. Blood, 1998, 92(1), 40-45).

Compounds of the invention will be further useful to reduce elevated intra-ocular pressure of a subject, e.g., through relaxation of pre-contracted isolated ciliary muscle.

In particular, a mammal such as a human suffering from or susceptible to glaucoma or other disorder associated with elevated intra-ocular pressure. Compounds of the invention also will be useful for treatment of a mammal, particularly a human, that is suffering from or susceptible to dry eye.

Compounds of the invention also will be useful for promoting sleep in a subject, e.g., to treat a mammal particularly a human suffering from or susceptible to a sleep disorder such as may be associated with advanced age, such as a human of 65 years or older.

Compounds of the invention also will be useful to treat a mammal suffering from or susceptible to a sexual dysfunction, particularly a human male suffering from erectile dysfunction.

Compounds of the invention also will be useful to treat a mammal suffering from or susceptible to an inflammatory disease or disorder including vascular inflammation, inflammatory pain and hyperalgesia.

Compounds of the invention will be further useful to treat a mammal suffering from or susceptible to ulcers, particularly gastric ulcers. Such therapies may be conducted in conjunction with a patient being treated with an anti-inflammatory agent, which can promote gastric ulcers.

Compounds of the invention also may be administered to a mammal particularly a human that is suffering from or susceptible to a skin disorder, particularly dry skin (ichthyosis) or skin rash.

In a further aspect, the invention provides a use of a pyrrolidin-2-one compound, including a compound particularly selected from the group consisting of any one of Formulae I through V for the treatment or prevention (including prophylactic treatment) of a disease or condition as disclosed herein, including pre-term labor, ovulation induction, cervical ripening, dysmenorrhea, asthma, hypertension, infertility or fertility disorder, undesired blood clotting, pre-eclampsia or eclampsia, an eosinophil disorder, sexual dysfunction including erectile dysfunction, osteoporosis and other destructive bone disease or disorder, renal dysfunction (acute and chronic), immune deficiency disorder or disease, dry eye, skin disorders such as ichthyosis, elevated intra-ocular pressure such as associated with glaucoma, sleep disorders, ulcers, inflammatory diseases or disorders and other diseases and disorders associated with the prostaglandin and receptors thereof.

In a yet further aspect, the invention provides a use of a pyrrolidin-2-one compound, particularly a compound of any one of Formulae I through V for the preparation of a medicament for the treatment or prevention (including prophylactic treatment) of a disease or condition as disclosed herein, including pre-term labor, ovulation induction, cervical ripening, dysmenorrhea, asthma, hypertension, infertility or fertility disorder, undesired blood clotting, pre-eclampsia or eclampsia, an eosinophil disorder, sexual dysfunction, including erectile dysfunction, osteoporosis and other destructive bone disease or disorder, renal dysfunction (acute and chronic), immune deficiency disorder or disease, dry eye, skin disorders such as ichthyosis, elevated intra-ocular pressure such as associated with glaucoma, sleep disorders, ulcers, inflammatory diseases or disorders and other diseases and disorders associated with the prostaglandin and receptors thereof.

Preferred methods of the invention including identifying and/or selecting a subject (e.g., mammal, particularly human) that is susceptible to or suffering from a condition disclosed herein, and thereafter administering to the identified and selected subject one or more compounds of the invention, particularly a subject that is identified and selected as being susceptible to or suffering from infertility, particularly anovulatory disorders, pre-term labor, asthma, hypertension, sexual dysfunction, including erectile dysfunction, osteoporosis and other destructive bone disease or disorder, inflammation, renal dysfunction (acute and chronic), immune deficiency disorder or disease, dry eye, skin disorders such as ichthyosis, elevated intra-ocular pressure such as associated with glaucoma, sleep disorders, ulcers, or other diseases and disorders associated with prostaglandin.

The invention also provides pharmaceutical compositions that comprise one or more of the pyrrolidin-2-one compounds of the invention together with a suitable carrier for the compound (s).

In a further aspect, the invention provides methods and pharmaceutical compositions comprising administering a prostaglandin $DP_1$ receptor agonist for the treatment of infertility, including ovulatory disorders. More specifically, the present invention relates to such methods and pharmaceutical compositions for inducing ovulation, including ovulation triggering: more specifically, for triggering ovulation in a patient under a treatment for ovulation induction or under ART (Assisted Reproductive Technology) therapies.

In a yet further aspect, the invention provides methods and pharmaceutical compositions comprising administering a prostaglandin $DP_1$ receptor agonist for the treatment of infertility disorders wherein the $DP_1$ agonist is selected among compounds of following Formula VI:

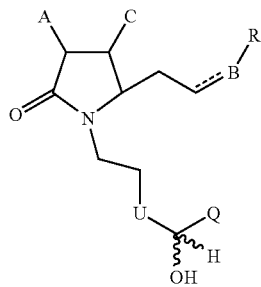

VI wherein A an C are each independently H or OH, and preferably are each H;

B is selected from the group comprising or consisting of optionally substituted $C_1$-$C_6$ alkyl, preferably $C_3$ or $C_4$ alkyl, optionally substituted aryl $C_1$-$C_6$ alkyl, optionally substituted aryl $C_1$-$C_6$ heteroalkyl, preferably aryl $C_1$-$C_6$ alkoxy, optionally substituted heteroaryl $C_1$-$C_6$ alkoxy, optionally substituted aryl, optionally substituted heteroaryl, optionally substituted $C_3$-$C_6$ cycloalkyl and optionally substituted $C_3$-$C_6$ heterocycloalkyl, provided that when B is optionally substituted aryl, optionally substituted heteroaryl, optionally substituted $C_3$-$C_6$ cycloalkyl and optionally substituted $C_3$-$C_6$ heterocycloalkyl, the undefined bond linking B is a single bond;

The dotted line indicates an optional double bond;

R is C(=O) Z wherein Z is selected from the group comprising or consisting of hydrogen, hydroxy, alkoxy such as —O-alkyl preferably —O—$C_1$-$C_4$ alkyl (i.e., to provide $C_1$-$C_4$ ester, including methyl, ethyl, propyl or butyl esters), optionally substituted alkyl, preferably $C_1$-$C_6$ alkyl and optionally substituted aryl; or Z is selected from the group comprising or consisting of amino or alkylamine such as —$NR^1R^2$ wherein $R^1$ and $R^2$ are independently selected from hydrogen and optionally substituted alkyl, preferably $C_1$-$C_6$ alkyl, —$NHSO_2R^3$ and —$NHC(O)R^3$ wherein $R^3$ is selected among optionally substituted $C_1$-$C_6$ alkyl and optionally substituted aryl; or R is optionally substituted heteroaryl, preferably including at least one N atom, including tetrazolyl;

U is $(CH_2)$ p wherein p is an integer selected from 0, 1 and 2, preferably 0 or 1;

Q is —$CR^4R^5$-W, wherein $R^4$ and $R^5$ are independently selected from H, halogen and optionally substituted $C_1$-$C_6$ alkyl; or $R^4$ and $R^5$ can form an optionally substituted $C_3$-$C_6$ cycloalkyl with the carbon they are attached to, preferably an optionally substituted $C_3$, $C_4$ or $C_5$ cycloalkyl;

W is selected from the group comprising or consisting of hydrogen, optionally substituted $C_1$-$C_6$ alkyl, optionally substituted $C_3$-$C_6$ cycloalkyl, optionally substituted $C_3$-$C_6$ heterocycloalkyl, optionally substituted $C_3$-$C_6$ cycloalkyl $C_1$-$C_6$ alkyl, optionally substituted $C_3$-$C_6$ heterocycloalkyl $C_1$-$C_6$ alkyl, optionally substituted aryl, optionally substituted heteroaryl, optionally substituted aryl $C_1$-$C_6$ alkyl and optionally substituted heteroaryl $C_1$-$C_6$ alkyl; and pharmaceutically acceptable salts thereof.

Preferred said $DP_1$ agonists are selected in an $DP_1$ binding assay. An example of such an assay is defined in Example 5 below.

The pyrrolidin-2-one derivatives described herein may contain a variety of substituent groups. Suitable alkyl substituent groups of compounds of the invention (which includes compounds of Formulae I, II, III, IV and V, and variants thereof described herein) typically have from 1 to about 12 carbon atoms, more preferably 1 to about 8 carbon atoms, still more preferably 1, 2, 3, 4, 5, or 6 carbon atoms. As used herein, the term "alkyl," unless otherwise modified, refers to both cyclic and noncyclic as well as branched and straight groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2, 3, 4, 5, or 6 carbon atoms. The terms alkenyl and alkynyl as used herein refer to both cyclic and noncyclic groups, although straight or branched noncyclic groups are generally more preferred.

Preferred alkoxy groups of compounds of the invention include groups having one or more oxygen linkages and from 1 to about 8 carbon atoms, and still more preferably 1, 2, 3, 4, 5 or 6 carbon atoms. Preferred alkylamino groups include those groups having one or more primary, secondary and/or tertiary amine groups, and from 1 to about 8 carbon atoms, still more preferably 1, 2, 3, 4, 5, or 6 carbon atoms.

Suitable heteroalicyclic groups of compounds of the invention particularly as substituent B of Formula I, contain one or more N, O or S atoms and include, e.g., tetrahydrofuranyl, thienyl, piperidinyl, morpholino and pyrrolidinyl groups.

Suitable heteroaromatic groups of compounds of the invention particularly as substituent B of Formula I are 5-membered or 6-membered single ring moieties having at least one of N, O or S rings atoms. Particular examples of heteroaromatic groups include optionally substituted pyridyl, pyrrolyl, furyl (furanyl), thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido [3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl. Optionally substituted thienyl, optionally substituted furanyl, optionally substituted pyrazinyl and optionally substituted pyridyl are particularly preferred heteroaromatic B substituents.

Suitable carbocyclic aryl groups of compounds of the invention include single and multiple ring compounds, including multiple ring compounds that contain separate and/ or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including phenyl, 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,4-substituted phenyl, and 2,5-substituted phenyl; and substituted naphthyl, including naphthyl substituted at the 5, 6 and/or 7 positions.

Suitable aralkyl groups of compounds of the invention include single and multiple ring compounds, including multiple ring compounds that contain separate and/or fused carbocyclic aryl groups. Typical aralkyl groups contain 1 to 3 separate or fused rings and from 6 to about 18 carbon ring atoms. Preferred aralkyl groups include benzyl and naphthylmethyl (—CH$_2$-naphthyl), and other carbocyclic aralkyl groups, as discussed above.

As discussed above, various substituents of the above formulae, such as R, R1, R, B, V, Q, and Z may be optionally substituted. A "substituted" R, R1, R2, B, V, Q, and Z group or other substituent may be substituted by other than hydrogen at one or more available positions, typically 1 to 3 or 4 positions, by one or more suitable groups such as those disclosed herein. Suitable groups that may be present on a "substituted" R, R$^1$, R$^2$, B, V, Q, and Z group or other substituent include e.g. halogen such as fluoro, chloro, bromo and iodo; cyano; hydroxyl; nitro; azido; alkanoyl such as a C$_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups including those having one or more oxygen linkages and from 1 to about 12 carbon atoms, or 1, 2, 3, 4, 5 or 6 carbon atoms; aryloxy such as phenoxy; alkylamino groups such as groups having one or more N atoms and from 1 to about 12 carbon atoms, or 1, 2, 3, 4, 5 or 6 carbon atoms; carbocyclic aryl having 6 or more carbons; aralkyl having 1 to 3 separate or fused rings and from 6 to about 18 carbon ring atoms, with benzyl being a preferred group; or aralkoxy having 1 to 3 separate or fused rings and from 6 to about 18 carbon ring atoms, such as O-benzyl. Also comprised by the term optionally substituted shall be situations where at one position of a moiety R, R$^1$, R$^2$, B, V, Q, Z two alkyl substituents undergo ring closure to provide for a cycloalkyl, e.g. a cyclopropyl, moiety.

A particularly preferred embodiment of the invention is the group of pyrrolidine derivatives according to formula V wherein R is —C(O)OH being in a "para" position whereby n is 1.

Q is selected from the group comprising or consisting of optionally substituted C$_1$-C$_6$ alkyl, preferably butyl, pentyl, hexyl, methyl butyl, methyl propyl, di-methyl propyl, di-methyl pentyl or trifluoropropyl, optionally substituted C$_2$-C$_6$ alkenyl, preferably butenyl, optionally substituted C$_2$-C$_6$ alkynyl and —CR$^1$R$^2$-W, wherein R$^1$ and R$^2$ are independently selected from H and optionally substituted C$_1$-C$_6$ alkyl, preferably H or methyl; or R$^1$ and R$^2$ can form an optionally substituted C$_3$-C$_6$ cycloalkyl with the carbon they are attached to, preferably an optionally substituted C$_3$ or C$_4$ cycloalkyl, preferably cyclopropyl or cyclobutyl; W is selected from the group comprising or consisting of hydrogen, optionally substituted C$_1$-C$_6$ alkyl, preferably propyl, butyl, pentyl, methyl-1-ethyl, methyl propyl, tert-butyl or tri-fluoro ethyl, optionally substituted C$_3$-C$_6$ cycloalkyl C$_1$-C$_6$ alkyl, preferably, methyl cyclopropyl, ethyl cyclopropyl, optionally substituted C$_3$-C$_6$ cycloalkyl, preferably cyclopropyl, cyclopentyl or cyclohexyl, optionally substituted aryl, preferably optionally substituted phenyl including phenyl, methyl phenyl, halogeno phenyl and chloro phenyl and optionally substituted aryl C$_1$-C$_6$ alkyl, preferably ethyl phenyl; and pharmaceutically acceptable salts thereof.

Another more preferred group of compounds of the invention includes compounds of formula V wherein R is —C(O)OH being in a "para" position whereby n is 1; Q is —CR$^1$R$^2$-W, wherein R$^1$ and R$^2$ are independently selected from H and optionally substituted C$_1$-C$_6$ alkyl, preferably H or methyl; or R$^1$ and R$^2$ can form an optionally substituted C$_3$-C$_6$ cycloalkyl with the carbon they are attached to, preferably an optionally substituted C$_3$ or C$_4$ cycloalkyl, preferably cyclopropyl or cyclobutyl; W is selected from the group comprising or consisting of hydrogen, optionally substituted C$_1$-C$_6$ alkyl, preferably propyl, butyl, pentyl, optionally substituted C$_3$-C$_6$ cycloalkyl C$_1$-C$_6$ alkyl, preferably methyl cyclopropyl or ethyl cyclopropyl and optionally substituted aryl, preferably optionally substituted phenyl including phenyl and methyl phenyl; and pharmaceutically acceptable salts thereof.

Specifically preferred pyrrolidinones of the invention include the following depicted compounds and pharmaceutically acceptable salts of these compounds:

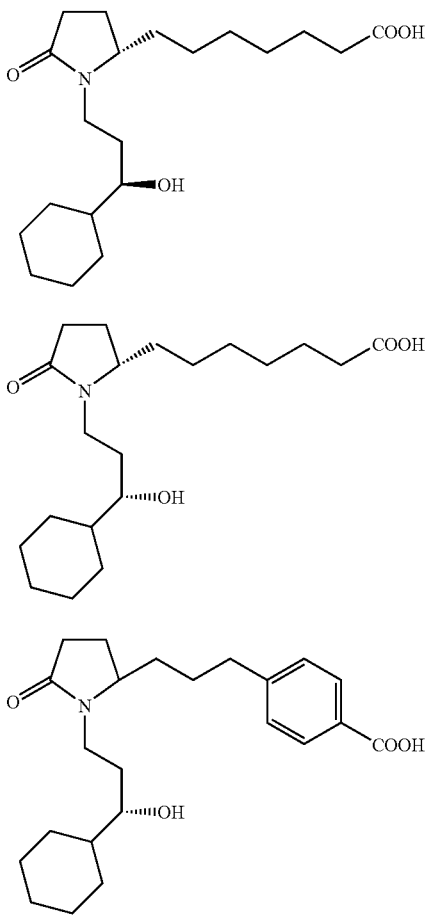

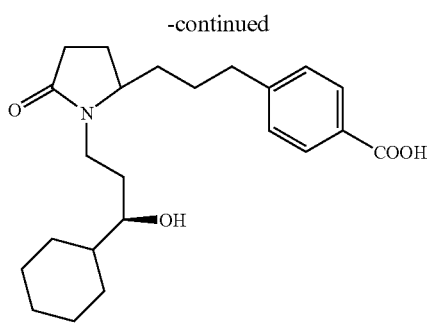
In addition to the foregoing exemplary compounds, other useful DP₁ agonists of the invention include but are not limited to
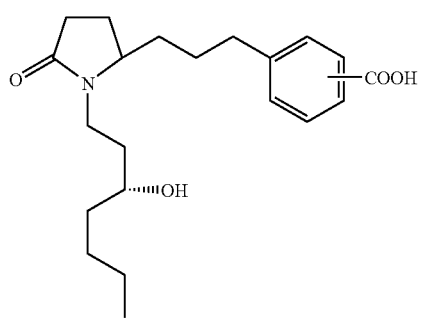
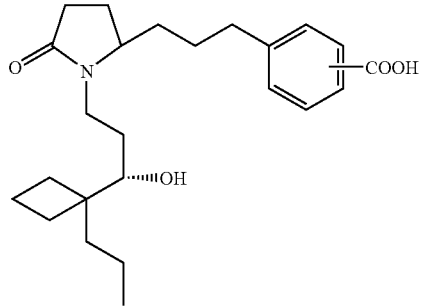
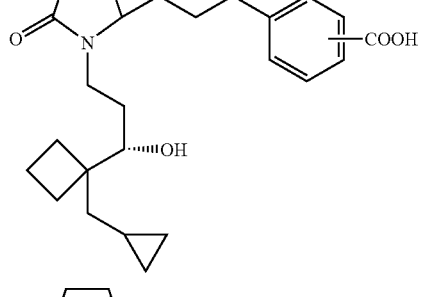
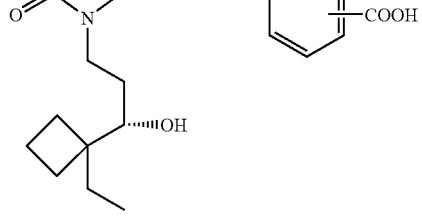
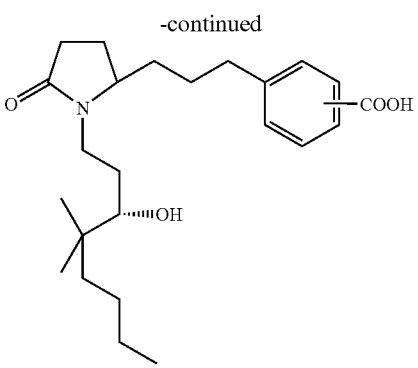
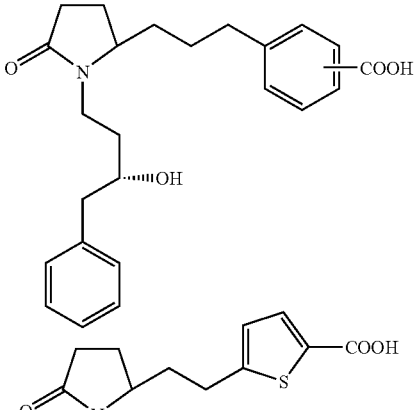
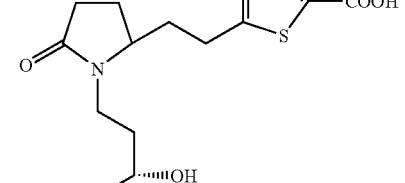
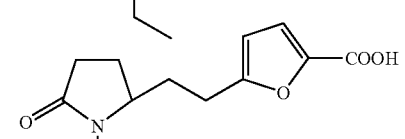
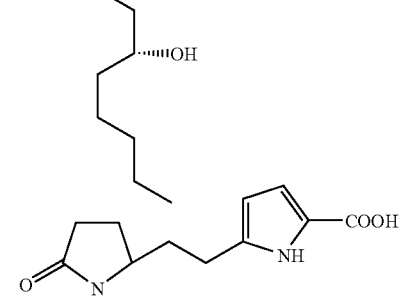
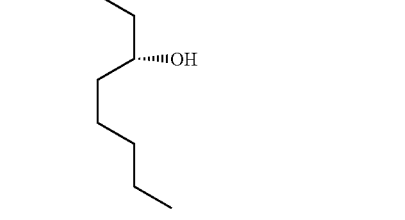

-continued
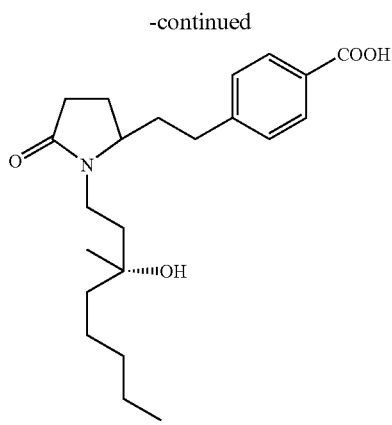
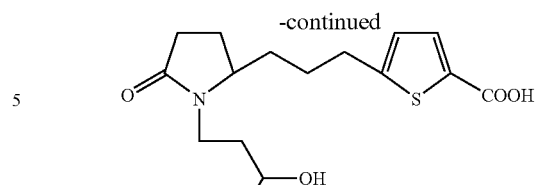
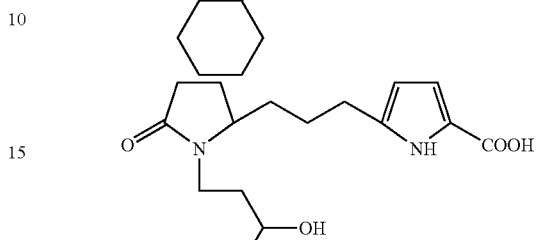
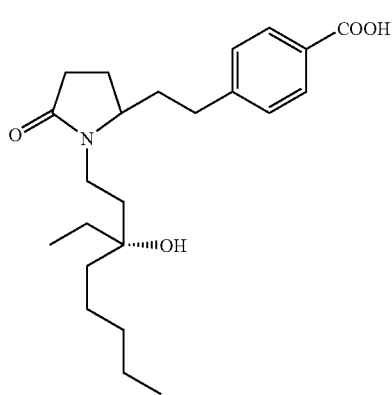
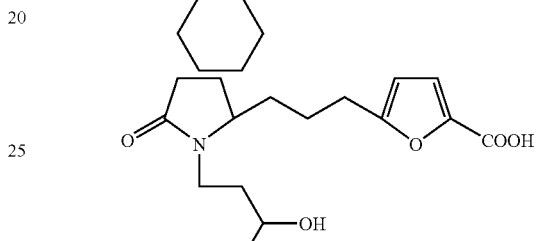
Other preferred structures include:
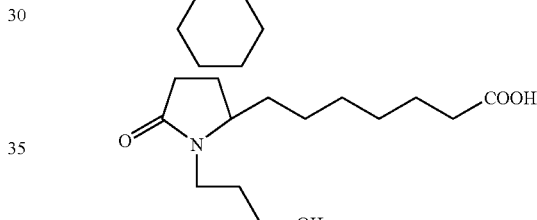
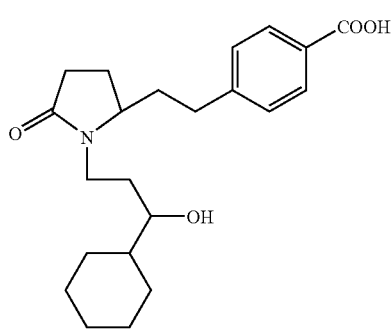
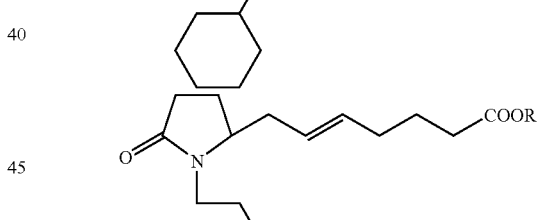
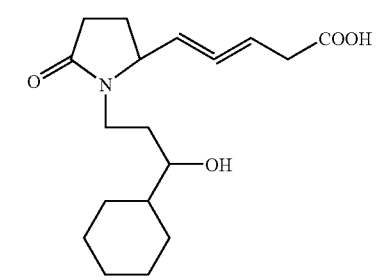
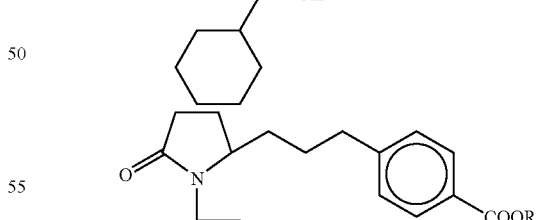
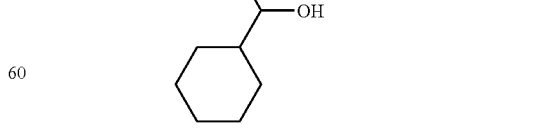
where R is a H, an alkyl group or an aryl group forming an ester or a salt.
As discussed above, preferred compounds of the invention exhibit activity in a prostaglandin $DP_1$ receptor binding assay as described, for example in the protocol of Example 5 which follows. Generally preferred compounds of the invention have a Ki(µM) of about 100 or less, more preferably about 50 or less, still more preferably a Ki(µM) of about 10 or 20 or less, even more preferably a Ki(pM) of about 5 or less in such a prostaglandin assay as exemplified by Example 5 provided herein below.

The pyrrolidinone compounds of the invention can be readily prepared. Suitable synthetic procedures are exemplified in the following Scheme 1. It should be appreciated that the compounds shown in the following Scheme are exemplary only, and a variety of other compounds can be employed in a similar manner as described below.

In another aspect of the invention, are provided methods and pharmaceutical compositions comprising administering a prostaglandin $DP_1$ receptor agonist for the treatment of infertility, including ovulatory disorders. More specifically, the present invention relates to such methods and pharmaceutical compositions for inducing ovulation, particularly ovulation triggering; more specifically, the present invention relates to such methods and pharmaceutical compositions for triggering ovulation in patients under ovulation induction or ART treatments.

The term "$DP_1$ receptor agonist" refers to a compound, including its isomers, pro-drugs and pharmaceutically acceptable salts, which bind to the prostaglandin $DP_1$ sub-type receptor. A prostaglandin $DP_1$ sub-type agonist can be identified by several conventional assays, including a prostaglandin $DP_1$ binding assay and a cyclic AMP assay on cells over-expressing $DP_1$ receptor. Other appropriate conventional assays may be used by the skilled person in the art for selecting $DP_1$ agonists.

Preferred prostaglandin $DP_1$ receptor agonists exhibit activity in a prostaglandin $DP_1$ receptor binding assay, an example thereof is defined in the protocol as defined in Example 5 provided herein below.

A particularly preferred group of $DP_1$ receptor agonists of the invention have a Ki(nM) of about 20 or less, more preferably about 10 or less, still more preferably a Ki (nM) of about 5 or 2 or less, even more preferably a Ki(nM) of about 1 or less, further more preferred, a Ki(nM) of about 0.1 or less in a prostaglandin $DP_1$ receptor binding assay as exemplified by Example 5 which follows.

Other preferred prostaglandin $DP_1$ receptor agonists exhibit activity in a cAMP assay on cell lines over-expressing $DP_1$ receptor, an example thereof is defined in the protocol as defined in Example 5, which follows.

Another particularly preferred group of $DP_1$ receptor agonists of the invention have a $EC_{50}$ (nM) of about 30 or less, more preferably about 20 or less, still more preferably a $EC_{50}$ (nM) of about 10 or 5 or less, even more preferably a $EC_{50}$ (nM) of about 1 or 0.1 less in such a cAMP/$DP_1$ receptor as exemplified by Example 5, which follows.

In a further embodiment of the invention, the selective $DP_1$ receptor agonists used for triggering ovulation can be selected from $DP_1$ agonists described in the art that have the preferred $DP_1$ activities mentioned above in $DP_1$ assays.

In one embodiment of the invention, the said method for inducing ovulation is a method wherein said $DP_1$ agonist is selected among compounds of Formula VI, wherein the substituents A, B, D, R, U, Q, W, $R^1$, $R^2$, $R^3$, $R^4$ and $R^5$ are the same as defined in Formula VI above.

In one preferred embodiment of the invention, the said method for triggering ovulation for ovulation induction or ART is a method wherein said $DP_1$ agonist is selected among compounds of formula VI, wherein A is H; B is optionally substituted $C_1$-$C_6$ alkyl, preferably butyl; D is a double bond; R is C(=O)Z wherein Z is selected from hydrogen, hydroxy, alkoxy such as —O-alkyl preferably —O—$C_1$-$C_4$ alkyl (i.e., to provide $C_1$-$C_4$ ester, including methyl, ethyl, propyl or butyl esters) and optionally substituted alkyl, preferably $C_1$-$C_6$ alkyl; or Z is selected from amino or alkylamine such as —$NR^1R^2$ where $R^1$ and $R^2$ are independently hydrogen or optionally substituted alkyl, preferably $C_1$-$C_6$ alkyl, —$NHSO_2R^3$ and —$NHC(O)R^3$ wherein $R^3$ is selected among optionally substituted $C_1$-$C_6$ alkyl and optionally substituted aryl; U is $(CH_2)p$ wherein p is 0; Q is —$CR^4R^5$-W, wherein $R^4$ and $R^5$ are independently selected from H, halogen and optionally substituted $C_1$-$C_6$ alkyl; W is selected from optionally substituted $C_3$-$C_6$ cycloalkyl, optionally substituted $C_3$-$C_6$ heterocycloalkyl, optionally substituted aryl and optionally substituted heteroaryl; and pharmaceutically acceptable salts thereof.

In another preferred embodiment of the invention, the method for triggering ovulation for ovulation induction or ART is a method wherein agonist used is selected among compounds of formula VI, wherein A is H; B is optionally substituted $C_1$-$C_6$ alkyl, preferably $C_3$ or $C_4$ alkyl; D is single or cis double bond; R is C(=O)Z wherein Z is selected from hydrogen, hydroxy, alkoxy such as —O-alkyl, preferably —O—$C_1$-$C_4$ alkyl (i.e., to provide $C_1$-$C_4$ ester, including methyl, ethyl, propyl or butyl esters); or R is optionally substituted heteroaryl, preferably including at least one N atom, including tetrazolyl; U is $(CH_2)$ p wherein p is 0; Q is —$CH_2$-W, wherein W is selected from optionally substituted $C_3$-$C_6$ cycloalkyl, optionally substituted $C_3$-$C_6$ heterocycloalkyl, optionally substituted aryl and optionally substituted heteroaryl; and pharmaceutically acceptable salts thereof.

In another preferred embodiment of the invention, the method triggering ovulation for ovulation induction or ART is a method that uses a $DP_1$ agonist selected among compounds of formula VI, wherein A is H; B is selected from optionally substituted aryl $C_1$-$C_6$ alkoxy, preferably aryloxy, most preferably phenyloxy, optionally substituted-$CH_2$-aryl and optionally substituted-$CH_2$-heteroaryl; D is a single bond; R is C(=O)Z wherein Z is selected hydrogen, hydroxy and alkoxy such as —O-alkyl, preferably —O—$C_1$-$C_4$ alkyl (i.e., to provide $C_1$-$C_4$ ester, including methyl, ethyl, propyl or butyl esters); or R is optionally substituted heteroaryl, preferably including at least one N atom, including tetrazolyl; U is $(CH_2)$ p wherein p is 0; Q is —$CH_2$-W, wherein W is selected from optionally substituted $C_3$-$C_6$ cycloalkyl, optionally substituted $C_3$-$C_6$ heterocycloalkyl, optionally substituted aryl and optionally substituted heteroaryl; and pharmaceutically acceptable salts thereof.

In another preferred embodiment of the invention, the said method for triggering ovulation for ovulation induction or ART is a method wherein said $DP_1$ agonist is selected among compounds of formula VI, wherein A is H; B is optionally substituted aryl, preferably phenyl; D is a single bond; R is C(=O)Z wherein Z is hydroxy; U is $(CH_2)p$ wherein p is 0; Q is —$CR^4R^5$-W, wherein $R^4$ and $R^5$ are independently selected from H and optionally substituted $C_1$-$C_6$ alkyl, preferably H or methyl; or $R^4$ and $R^5$ can form an optionally substituted $C_3$-$C_6$ cycloalkyl with the carbon they are attached to, preferably an optionally substituted $C_3$ or $C_4$ cycloalkyl; W is selected from optionally substituted $C_1$-$C_6$ alkyl, preferably methyl propyl, butyl, pentyl, optionally substituted $C_3$-$C_6$ cycloalkyl $C_1$-$C_6$ alkyl, preferably methyl cyclopropyl, ethyl cyclopropyl, optionally substituted $C_3$-$C_6$ cycloalkyl, preferably cyclopropyl, cyclopentyl, optionally substituted aryl, preferably optionally substituted phenyl; and pharmaceutically acceptable salts thereof.

Specifically preferred DP$_1$ agonists of the invention for triggering ovulation for ovulation induction or ART, include the following depicted compounds and pharmaceutically acceptable salts of these compounds:

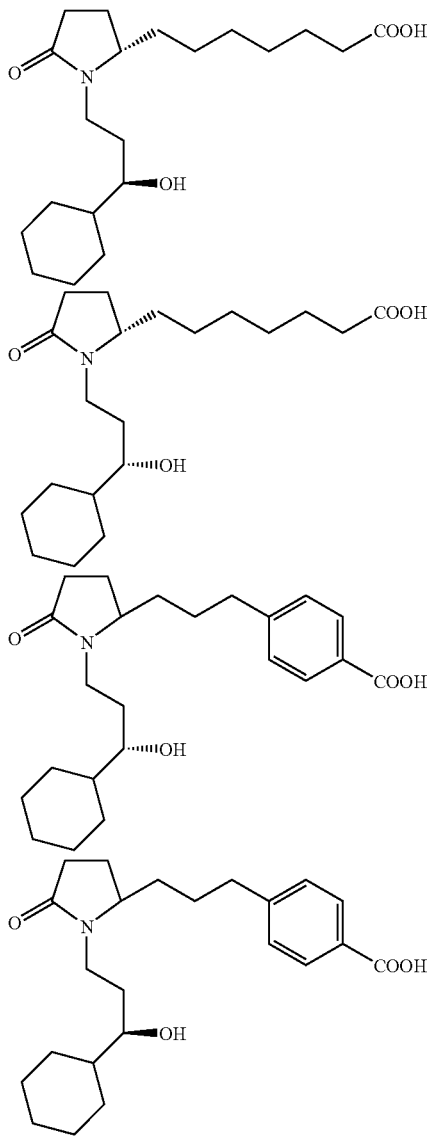

The term "C$_1$-C$_6$-alkyl" refers to monovalent branched or unbranched alkyl groups having 1 to 6 carbon atoms. Examples of alkyl groups that are encompassed by this term include but are not limited to groups such as methyl, ethyl, n-propyl, isopropyl, n-butyl, isobutyl, tert-butyl, n-hexyl and the like. By analogy, the term "C$_1$-C$_4$-alkyl" refers to monovalent branched or unbranched alkyl groups having 1 to 4 carbon atoms. Examples of alkyl groups that are encompassed by this term include but are not limited to groups such as methyl, ethyl, n-propyl, isopropyl, n-butyl, isobutyl, tert-butyl and the like.

The term "C$_1$-C$_6$-heteroalkyl" refers to a C$_1$-C$_6$-alkyl group according to the definition above, in which at least one carbon atom is replaced by heteroatoms chosen from the group consisting of O, S—NR, R being defined as hydrogen or methyl. Preferred C$_1$-C$_6$— heteroalkyl include methoxy methyl, methoxyethyl, methoxybutyl, and the like.

The term "C$_2$-C$_6$-alkenyl" refers to alkenyl groups preferably having from 2 to 6 carbon atoms and having at least 1 or 2 sites of alkenyl unsaturation. Preferable alkenyl groups include ethenyl (—CH═CH2), n-2-propenyl(allyl, —CH2CH═CH2) and the like.

The term "C$_2$-C$_6$-alkynyl" refers to alkynyl groups preferably having from 2 to 6 carbon atoms and having at least 1 or 2 sites of alkynyl unsaturation, preferred alkynyl groups include ethynyl, (—C≡CH), propargyl(—CH2C≡CH), and the like.

The terms "C$_2$-C$_6$-heteroalkenyl" and "C$_2$-C$_6$-heteroalkynyl" refer respectively to C$_2$-C$_6$-alkenyl and C$_2$-C$_6$-alkynyl, in which at least one carbon atom is replaced by heteroatoms chosen from the group consisting of O, S, NR, R being defined as hydrogen or methyl. Examples of C$_2$-C$_6$-heteroalkenyl include methoxy propenyl, methoxy butenyl, and the like. Examples of C$_2$-C$_6$-heteroalkynyl include methoxy propynyl, methoxy butynyl, and the like.

The term "C$_3$-C$_6$-cycloalkyl" refers to saturated carbocyclic rings having 3 to 6 carbon atoms. Examples include cyclopropyl, cyclobutyl, cyclopentyl, cyclohexyl, and the like. Unsaturated rings, e.g., cyclohexenyl also may be used.

The term "C$_3$-C$_8$ heterocycloalkyl" refers to a C$_3$-C$_8$-cycloalkyl group according to the definition above, in which up to 3 carbon atoms are replaced by heteroatoms chosen from the group consisting of O, S, and NR, R being defined as hydrogen or methyl.

Preferred heterocycloalkyl include pyrrolidine, piperidine, piperazine, 1-methylpiperazine, morpholine, and the like.

The term "C$_3$-C$_6$-cycloalkyl C$_1$-C$_6$-alkyl" refers to C$_1$-C$_6$-alkyl groups, as defined above, having saturated carbocyclic rings having 3 to 6 carbon atoms as substituent. Examples include ethyl cyclobutyl, cyclopropylmethyl cyclobutyl and the like.

The term "Aryl" refers to aromatic carbocyclic groups of from 6 to 14 carbon atoms having a single ring (e.g., phenyl) or multiple condensed rings (e.g., naphthyl). Examples include phenyl, naphthyl, phenanthrenyl and the like.

The term "Aryl C$_1$-C$_6$-alkyl" refers to C$_1$-C$_6$-alkyl groups having an aryl substituent, including benzyl, phenethyl and the like.

The term "pro-drug" refers to compounds that are drug precursors which, following administration release the drug in vivo via some chemical or physiological process.

The term "DP$_1$ agonist" refers to a compound, including its isomers, pro-drugs and pharmaceutically acceptable salts, which bind to prostaglandin DP$_1$ subtype receptor. Such property can be readily determined by those skilled in the art (for example, see Boie, Y. et al Eur. J. Pharmacol. 1997, 340, 227-241 or Abramovitz M. et al Biochim at Biophysica Acta 2000, 1483, 285-293). A variety of such compounds are described and referenced herein. However, other prostaglandin DP$_1$ agonists will be known to those skilled in the art. Exemplary DP$_1$ agonists are disclosed as follows.

The term "selective binding to the DP$_1$ receptor" refers to compounds that are selective in comparison to the other prostaglandin receptors, particularly DP$_2$, EP$_1$ and/or EP$_3$, optionally EP$_2$. Selectivity in this connection means that the affinity of the compounds of the invention for the DP$_1$ receptor is at least more than 2 times higher than the affinity for another prostaglandin receptor, more preferably, the affinity is at least 5 time higher, even more preferably the affinity is more than 10 times and in particular more than 100 or 1000 times the affinity for other prostaglandin receptors like $EP_1$ or $EP_3$ and at least more than 2 times, especially more than 10 times the affinity for the $DP_2$ receptor.

The term "fertility condition(s)" also refers to a condition, particularly infertility, of a female mammal, especially a female patient. This condition includes conditions where ovulation triggering is needed. Examples of female patients in such a condition are female undergoing a treatment for ovulation induction or an Assisted Reproductive Technology (ART) therapies.

The term "ovulation induction" (OI), refers to the stimulation of release of an oocyte (occasionally two or three oocytes) into the fallopian tubes of a female patient, for in vivo fertilisation. OI is used in anovulatory patients [for example, WHO group I patients (hypogonadotrophic hypogonadism) and WHO group II anovulation (hypothalamic-pituitary dysfunction resulting in arrested or attenuated gonadal function), including patients suffering from polycystic ovarian syndrome (PCOS)]. It is usually desired to stimulate the release of a single oocyte, in order to avoid the risks associated with multiple pregnancies. In a typical ovulation induction regimen, the patient is administered FSH, an analogue of FSH or a molecule stimulating endogenous FSH production to stimulate follicular growth for several days until at least one follicle is observed (by ultrasound) with a mean diameter of approximately 17 mm or greater. At this stage, an ovulation trigger (hCG) is given to stimulate rupture of the follicle and release of an oocyte into the fallopian tube ("ovulation triggering"). The molecules of the invention can replace or supplement the ovulation triggering dose of hCG in an OI regimen. Combination therapies using a combination of the compound of the present invention and one or more of the compounds traditionally employed in an OI regimen is specifically contemplated.

The term "Assisted Reproduction Technology" includes for example, in vitro fertilisation (IVF), and intracytoplasmic sperm injection (ICSI). Oocytes are harvested from mature follicles immediately before rupture, and graded before being fertilised in vitro by combination with sperm. The resulting embryos are graded for quality, and usually 2 to 3 are selected for placement in the uterus (remaining embryos can be cryopreserved for future attempts).

Because of the many factors involved in establishing an ongoing pregnancy, many patients must have oocytes placed in the uterus multiple times before success is achieved. Because of this, in contrast to OI regimens, for ART it is desired to harvest multiple oocytes, in order to maximise the chances of successful pregnancy. The controlled development of multiple preovulatory follicles by administration of exogenous agents capable of inducing follicular growth (such as FSH) is called controlled ovarian hyperstimulation (COH). When there are at least 3 follicles with a mean diameter greater than 16 mm, ovulation is triggered (hCG bolus). Oocytes are usually recovered from pre-ovulatory follicles, by aspiration. The molecules of the invention can replace or supplement the ovulation triggering dose of hCG in an ART regimen.

The invention will be described below by means of the following Examples, which should not be construed as in any way limiting the present invention.

Abbreviations

The following abbreviations are hereinafter used in the accompanying examples: min (minute), hr (hour), i. p. (intraperiotoneal), i. v. (intra-venous), mg (milligram), mmol (millimole), mM (millimolar), nM (nanomolar), eq (equivalents), mL (milliliter), µl (microliters), ACN (acetonitrile), BP (mean arterial pressure), BSA (Bovine Serum Albumin), cAMP (Cyclic adenosine monophosphate), DCM (dichloromethane), DMSO (dimethylsulfoxide), EtOAc (ethyl acetate), FBS (Foetal Bovine Serum), GP (Guinea Pig), hCG (human Chorionic Gonadotropin), HR (heart rate), IT (intratracheal), LPS (lipopolysaccharides), MES (2-[N-morpholino]ethanesulfonic acid), $MgSO_4$ (magnesium sulfate), NP3S (N-methyl-pyrrolidinone), PBS (Phosphate buffered saline), PEG (Polyethylene Glycol), PGE1 (Prostaglandin E1), PGE2 (Prostaglandin E2), PMSG (pregnant mare serum gonadotrophin), p. o. (per os, oral administration), PVT (polyvinyltoluene), PSS (physiologic salt solution), RT (room temperature), SPA (Scintillation proximity Assay), TFA (trifluoroacetic acid), THF (tetrahydrofuran), TNF (Tumour Necrosis factor).

Synthesis of Compounds of the Invention:

Compounds of the invention can be readily prepared from readily available starting materials using the following general methods and procedures.

Suitable synthetic procedures are exemplified in the following illustrative Scheme 1. It should be appreciated that the compounds shown in the following Scheme are exemplary only, and a variety of other compounds can be employed in a similar manner as described below. Further, each of the isolatable intermediates described herein are specifically noted as being useful starting materials and/or therapeutic compounds in themselves.

Compounds having non-hydrogen substituents at the 4 and 5 ring positions can be provided using a starting reagent having such substitution. It will also be appreciated that where typical or preferred experimental conditions (i.e., reaction temperatures, time, moles of reagents, solvents etc.) are given, other experimental conditions can also be used unless otherwise stated. Optimum reaction conditions may vary with the particular reactants or solvents used. Such conditions can be determined by the person skilled in the art, using routine optimisation procedures.

The general synthesis of gamma-lactam derivatives acting as $DP_1$ selective agonists is described in schemes 1-3 below. Preparation of the benzyl prolinate derivative 6 was obtained as reported in scheme 1. Reaction of vinyl magnesium bromide with a suitable Weinreb amide 2 gave in good yield the desired enone derivative 3 that was used to alkylate H-D-Glu (OBn)-OBn via a Michael reaction. The ring closure product 5 was obtained via an intramolecular cyclization forming the amide bond by refluxing in the appropriate solvent for several hours. The pyrrolidin-2-one derivative contained the desired stereochemistry inherited from the unnatural aminoacid (D)-Glu derivative.

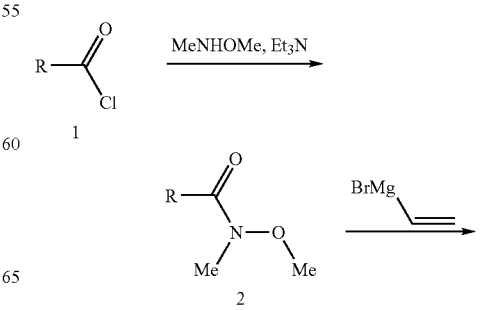

Scheme 1

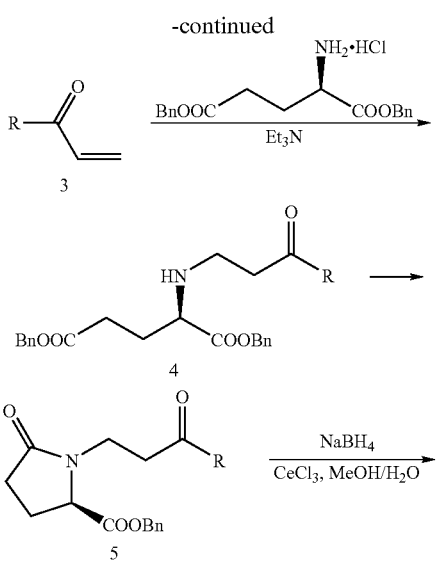

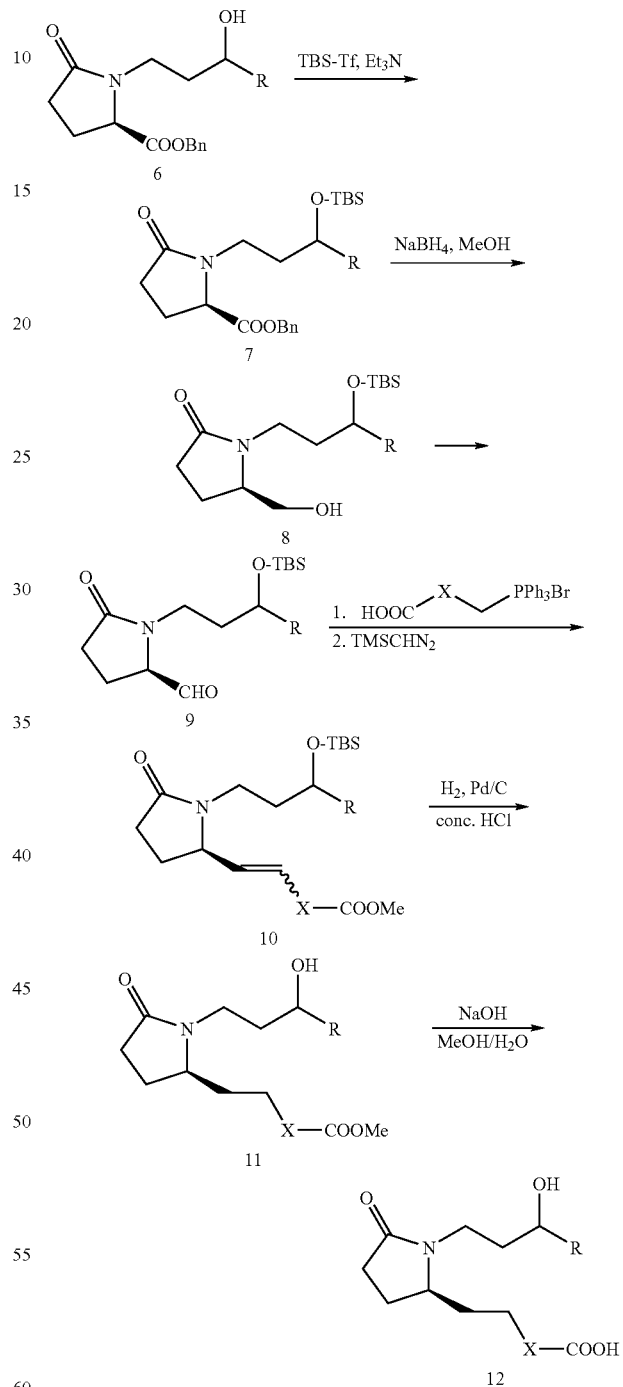

of the double bond under acidic conditions gave the alcohol intermediate 11. Saponification of the ester group gave in almost quantitative yield the desired pyrrolidin-2-one derivative.

The ketone 5 can be reduced nonspecifically via Luche's conditions using NaBH$_4$ and CeCl$_3$ in MeOH/H$_2$O. The resulting diastereoisomers can be isolated by column chromatography. Chiral reduction of the ketone intermediate could be obtained using the chiral reagent 2-methyl-CBS-oxazaborolodine and BH$_3$.THF complex at room temperature (scheme 2). The 2-methyl-CBS-oxazaborolodine is a chiral reagent and it should be understood that other chiral agents also may be used.

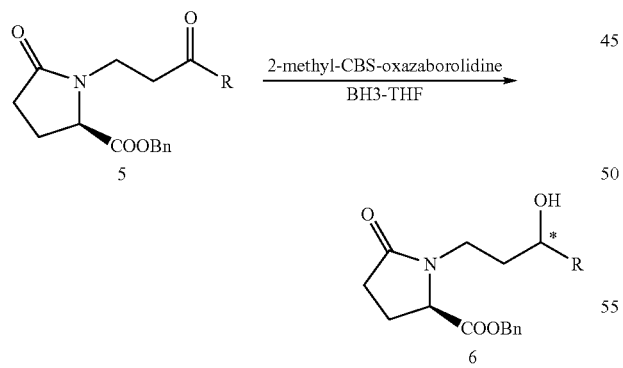

The synthesis of the final compounds was then carried out as described in Scheme 3. Protection of the alcohol moiety with a suitable protecting group like TBS followed by reduction of the ester group gave in good yield the pyrrolidin-2-one derivative 8. Swern oxidation of the primary alcohol gave the aldehyde intermediate 9. Wittig reaction using the desired phosphonate followed by the esterification of the acid intermediate yielded the intermediate 10. Catalytic hydrogenation Additional preferred syntheses of compounds of the invention are detailed in the examples provided below.

As indicated above, the present invention includes methods for treating or preventing prostaglandin mediated or associated diseases or disorders.

Preferred therapeutic methods of the invention include inhibiting undesired smooth muscle contraction, including undesired prostanoid-induced smooth muscle contraction. Methods of the invention include treatment of a patient suffering from or susceptible to dysmenorrhea, premature labor, asthma and other conditions that can be relieved by bronchodilation, inflammation, hypertension, undesired blood-clotting (e.g., to reduce or prevent thromboses) and other undesired platelet activities, preeclampsia and/or eclampsia and eosinophil-related disorders (eosinophil disorders).

Treatment and/or prevention of undesired blood clotting may include treatment and prophylaxis of venous thrombosis and pulmonary embolism, arterial thrombosis e.g., myocardial ischemia, myocardial infarction, unstable angina, stroke associated with thrombosis, and peripheral arterial thrombosis. Compounds of the invention also may be useful for anticoagulation involving artificial organs, cardiac valves, medical implementation (e.g., an indwelling device such as a catheter, stent, etc.) and the like.

The invention also includes methods for treatment of infertility, which generally comprise administration of one or more pyrrolidine compounds of the invention to a mammal, particularly a primate such as a human, suffering from or suspected of suffering from infertility. See the Merck Manual, vol. 2, pages 12-17(16th ed.) for identification of patients suffering from or suspected of suffering from infertility, which in the case of humans, can include failure to conceive within one year of unprotected intercourse.

The treatment methods of the invention may be particularly beneficial for female mammals suffering from an ovulatory disorder. Additionally, compounds of the invention can be administered to females undergoing assisted reproductive treatments such as in-vitro fertilization, e.g., to stimulate follicular development and maturation, as well as implantation procedures. In particular, treatment methods of the invention may be used in conjunction with in vitro fertilization technology to enhance survival and/or fertilization of a mammalian egg such as in IVF setting.

Treatment methods of the invention also may be employed for control of cervical ripening in late pregnancy (e.g., in humans, late pregnancy would be third trimester, particularly week 30 onward).

Therapeutic methods of the invention also include treatment of glaucoma or other disorder involving elevated intra-ocular pressure.

Treatment methods of the invention also include inhibition or prevention of bone loss such as to treat osteoporosis, and for promoting bone formation (e.g., to use as a therapy in a bone fracture) and other bone diseases such as Paget's disease. The invention also includes methods for treating a mammal that has low bone mass, or is susceptible to low bone mass such as a mammal having a condition that can present low bone mass, e.g., osteoporosis.

The invention also includes therapeutic methods for other bone mass augmentation treatments or enhancement, such as enhancing bone graft success rates or replacement of the need of such grafts, bone extension, bone healing following facial reconstruction and other treatments. Such treatment also may be used in coordination with an appropriate medical device, such as an orthopedic device e.g., a spinal case, bone pins and screws, and other bone fixation devices.

In general, such therapies are useful for any condition which can present low bone mass, which conditions include those where the level of bone mass is below the age specific normal as defined in standards by the World Health Organization "Assessment of Fracture Risk and its Application to Screening for Postmenopausal Osteoporosis (1994), World Health Organization Technical Series 843." More particularly, such conditions include periodontal disease, alveolar bone loss, post-osteotomy and childhood idiopathic bone loss, and primary and second osteoporosis as discussed above and complications thereof such as curvature of the spine, loss of height and prosthetic surgery.

Subjects particularly suitable for such bone growth promotion therapies include subjects suffering from acute injuries that can involve bone damage, subjects having undergone related surgery such as facial reconstruction, and subjects that are at increased risk of the above discussed disorders and diseases such as post-menopausal women and men and women over the age of 50 or 60.

Compounds of the invention also will be useful to treat sexual dysfunction, including male sexual dysfunction, such as erectile dysfunction.

Compounds of the invention also are useful for treatment of a subject suffering from or susceptible to renal dysfunction, including a mammal suffering from or susceptible to acute or chronic renal failure. Such treatment methods can promote repair and/or regeneration of kidney tissue in a mammal, particularly a human.

Compounds of the invention also are useful for treatment of a subject suffering from or susceptible to an immune disorder including an immune deficiency disease or disorder, including such a disorder associated with a viral infection particularly a retroviral infection such as an HIV infection. Particularly benefited by such therapies will be a human suffering from or susceptible to AIDS.

Compounds of the invention will be further useful to reduce elevated intra-ocular pressure of a subject, e.g., through relaxation of pre-contracted isolated ciliary muscle. In particular, a mammal such as a human suffering from, or susceptible, to glaucoma or other disorder associated with elevated intra-ocular pressure may be treated by the compounds of the present invention. Compounds of the invention also will be useful for treatment of a mammal, particularly a human that is suffering from or susceptible to dry eye.

Compounds of the invention will be further useful for treatment of a subject suffering from or susceptible to inflammatory diseases or disorders, including vascular inflammation, inflammatory pain and hyperalgesia.

Compounds of the invention also will be useful for promoting sleep in a subject, e.g., to treat a mammal particularly a human suffering from or susceptible to a sleep disorder such as may be associated with advanced age, such as a human of 65 years or older.

The therapeutic methods of the invention generally comprise administration of an effective amount of one or more compounds of the invention to a subject including a mammal, such as a primate, especially a human, in need of such treatment.

Typical candidates for treatment in accordance with the methods of the invention are persons suffering from or suspected of suffering from any of the above disorders or diseases, such as a female susceptible or suffering from preterm labor, or a subject suffering from or susceptible to dysmenorrhea or undesired bone loss.

The treatment methods of the invention also will be useful for treatment of mammals other than humans, including for veterinary applications such as to treat horses and livestock e.g., cattle, sheep, cows, goats, swine and the like, and pets such as dogs and cats. Methods of the invention to treat premature labor will be particularly useful for such veterinary applications. Therapeutic methods of the invention also will be useful for treatment of infertility in such veterinary applications.

For diagnostic or research applications, a wide variety of mammals will be suitable subjects including rodents (e.g., mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Compounds of the invention, including 1,2-substituted 5-pyrrolidinone compounds and $DP_1$ agonists, may be administered as a "cocktail" formulation with other therapeutics, i.e. coordinated administration for simultaneous, sequential or separate use, of one or more compounds of the invention together with one or more other active therapeutics, particularly one or more other known fertility agents. For instance, one or more compounds of the invention may be administered in coordination for simultaneous, sequential or separate use, with a regime of a pain relief agent, an anti-inflammatory agent, or an anti-coagulant, depending on the indication being treated.

Suitable anti-coagulants for such coordinated drug therapies include e.g., warfarin, heparin, hirudin or hirulog or an antiplatelet such as ReoPro.

For treatment of fertility disorders, one or more compounds of the invention, may be suitably administered in coordination, for simultaneous, sequential or separate use, with known fertility agents such as Follicle Stimulating and/or Leutinizing Hormone such as Gonal-F, Metrodin HP or Pergonal.

Compounds of the invention, including 1,2-substituted 5-pyrrolidinone compounds and $DP_1$ agonists, may be administered either as the sole active therapeutic or in a coordinated regime with one or more other therapeutics can be administered by a variety of routes, such as orally or by injection, e.g., intramuscular, intraperitoneal, subcutaneous or intravenous injection, or topically such as transdermally, vaginally and the like. Pyrrolidine compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g., a carboxy group, base addition salts may be prepared. Lists of additional suitable salts may be found, e.g., in Part 5 of Remington's Pharmaceutical Sciences, 20th Edition, 2000, Marck Publishing Company, Easton, Pa.

Compounds of the invention can be employed, either alone or in combination with one or more other therapeutic agents as discussed above, as a pharmaceutical composition in a mixture with conventional excipients, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Pharmaceutical compositions of the invention may preferably include a compound of the invention, including a 1,2-substituted 5-pyrrolidinone compounds and $DP_1$ agonists, packaged together with instructions (written) for therapeutic use of the compound to treat e.g., premature labor, dysmenorrhea or asthma, or other disorder as disclosed herein, such as a disease or disorder associated with or mediated by prostaglandin.

For oral administration, pharmaceutical compositions containing one or more compounds of the invention, including substituted pyrrolidine compounds and $DP_1$ agonists, may be formulated as e.g., tablets, troches, lozenges, aqueous or oily suspensions, dispersible powders or granules, emulsions, hard or soft capsules, syrups, elixirs and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular application, particularly suitable are solutions, preferably oily or aqueous solutions as well as suspensions, emulsions, or implants, including suppositories. Ampules are convenient unit dosages.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also Remington's Pharmaceutical Sciences, supra. In general, a suitable effective dose of one or more 1,2-substituted 5-pyrrolidinone compounds of the invention, particularly when using the more potent compound (s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several subdoses, e.g., 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage.

The entire text of all documents cited herein are incorporated by reference herein. The following non-limiting examples are illustrative of the invention. In the examples below, "rac." refers to a racemate or racemic mixture of the specified compound.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All reagents were used without additional purification, as received from commercial sources, Acros or Aldrich, unless stated otherwise. Anhydrous solvents were purchased from Acros in AcroSeal bottles. Silica Gel 230-400 mesh (Grade 60 Å) by Fisher Scientific was used for column chromatography. Silica Gel 60 $F_{254}$ Precoated Plates for Thin Layer Chromatography, layer thickness 250 µm, 2.5×7.5 cm were used for TLC analysis. Mass spectra were obtained with Finnigan LCQDuo LC/MSD spectrometer from Thermo-Quest. NMR spectra were obtained with Jeol Eclipse 400 spectrometer (400 MHz). Chemical shifts are given relative to TMS. Assignment of the NMR signals was made, where necessary, from C—H correlation and COSY spectra.

Example 1

Synthesis of 4-(3-(2S)-1-[(3R)-3-cyclohexyl-3-hydroxypropyl]-5-oxotetrahydro-1H-2-pyrrolylpropyl)benzoic acid

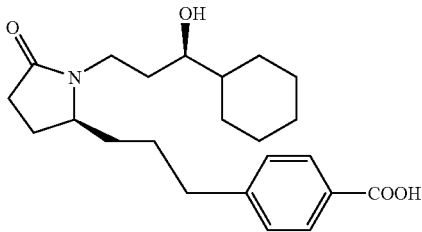

Intermediate 1.1:
4-Carboxyphenethyl(triphenyl)phosphonium bromide p-Bromoethylbenzoic acid (15 mmol, 3.45 g) and triphenylphosphine (16.5 mmol, 4.32 g) were refluxed in 100 ml m-xylene for 9 h (oil bath temperature 150° C.). The mixture was then cooled down, the solid formed was filtered, washed with m-xylene (2×20 ml), hexanes (2×20 ml), and air-dried to give 6.05 g (82%) of beige crystals. Recrystallization from MeOH—CHCl3-hexanes (~1:3:5) afforded 2.8 g (38%) of pure off-white crystals of 4-carboxyphenethyl(triphenyl)phosphonium bromide. $^1$H NMR (400 MHz, CDCl$_3$) δ 7.74 (d, 2H, 8.4 Hz, H2, H6 Ar), 7.68 (m, 3H, Ph$_3$P), 7.55 (m, 12H, Ph$_3$P), 7.09 (d, 2H, 8.4 Hz, H3, H5 Ar), 3.48 (m, 2H, CH$_2$—P), 2.86 (m, 2H, CH$_2$—Ar)

Intermediate 1.2:
N-Methyl-N-methoxy-cyclohexanecarboxamide

In a dried, flushed with nitrogen round bottom flask, N,O-dimethyl hydroxylamine hydrochloride (0.1 mol, 13.3 ml) was suspended in 200 ml anhydrous dichloromethane. To the resulting mixture triethylamine (0.22 mol, 30 ml) was added dropwise in ~5 min while cooling by water (stirring became difficult because of salts formation). To the resulting mixture, while stirring under nitrogen and cooling by ice water, cyclohexanecarbonyl chloride was added dropwise in ~15 min. The mixture was stirred overnight, washed with water (50 ml), saturated aqueous NH$_4$Cl (50 ml), then brine (50 ml), dried over Na$_2$SO$_4$, and concentrated to give 17.8 g of crude product. Purification on 150 g silica gel, eluent hexanes-ethyl acetate, from 100:0 to 50:50, afforded 13.6 g (80%) of N-methyl-N-methoxy-cyclohexanecarboxamide as clear oil, R$_f$ 0.44 (hexanes-EtOAc 1:1), $^1$H NMR (400 MHz, CDCl$_3$) δ 3.67 (s, 3H, OCH$_3$), 3.15 (s, 3H, NCH$_3$), 2.65 (m, 1H, CH—CO), 1.8-1.6 (m, 5H, cyclohexyl), 1.5-1.4 (qm, 2H, cyclohexyl), 1.3-1.2 (m, 3H, cyclohexyl).

Intermediate 1.3: 1-cyclohexylprop-2-en-1-one

To the stirring solution of N-methyl-N-methoxy-cyclohexanecarboxamide (0.05 mol, 8.5 g) in 150 ml anhydrous THF at –10-0° C. (ice-NaCl bath) the solution of vinyl magnesium bromide (1M in THF, 0.1 mol, 100 ml) was added dropwise. The resulting mixture was stirred at 0° C. for 1 h (white solid formed), then at rt for 4 h (the solid dissolved). The resulting solution was added slowly by cannula into a well-cooled Erlenmeyer flask equipped with magnetic stirrer and thermometer, containing 0.5 L saturated aqueous NH$_4$Cl, with such speed that the temperature stays between 0° C. and +10° C., at vigorous stirring. At higher temperatures oligomerization of the product occurs. The phases were separated; the aqueous one extracted with EtOAc (3×100 ml), and the combined organic extracts were washed with sat. aq. NH$_4$Cl until pH<7 (5×50 ml, carefully removing all the N,O-dimethylhydroxylamine product), then washed with brine (100 ml), dried with Na$_2$SO$_4$, and concentrated under vacuum >80 mbar (taking care not to evaporate the volatile product). Yield 11.8 g of yellow oil containing pure vinylcyclohexylketone. Used in the next reaction without purification as 0.05 mol. $^1$H NMR (400 MHz, CDCl$_3$) δ 6.41 (dd, 1H, 17.5 Hz, 10.3 Hz, Z—H—CH=C), 6.25 (dd, 1H, 17.5 Hz, 1.4 Hz, E-H—CH=C), 5.74 (dd, 1H, 10.3 Hz, 1.4 Hz, CO—CH=C), 2.60 (m, 1H, cyclohexyl CH—CO), 1.9-1.7 (m, 3H, cyclohexyl), 1.7-1.5 (m, 2H, cyclohexyl), 1.4-1.2 (m, 5H, cyclohexyl).

Intermediate 1.4: benzyl 1-(3-cyclohexyl-3-oxopropyl)-5-oxo-D-prolinate

In a flame-dried, nitrogen-flushed 1 L round bottom flask with magnetic stirrer, D-Dibenzyl glutamate hydrochloride (H-D-Glu(OBn)-OBn) (0.04 mol, 14.6 g) was dissolved in anhydrous 1-propanol (0.5 L). To the resulting solution cooled by ice bath, triethylamine (0.15 mol, 21 ml) was added at stirring under nitrogen. The mixture was stirred for 10 min followed by addition of freshly prepared vinylcyclohexylketone (0.05 mol). The reaction mixture was stirred under nitrogen at 0-5° C. for 3 h until reaction was complete (Control by LC-MS and NMR of concentrated aliquots).

When the reaction was complete, the cooling was removed, reflux condenser attached to the flask, and the mixture was refluxed overnight in an oil bath. The yellow solution was concentrated, diluted with a mixture of chloroform-hexanes (1:1 v/v, 100 ml), and filtered from white needles of Et$_3$NHCl. The filtrate was concentrated again giving 26.1 g of light yellow oil. Purification on 200 g of silica gel, eluent hexanes-EtOAc from 100:0 to 0:100, gave 8.85 g (62%) of pure benzyl 1-(3-cyclohexyl-3-oxopropyl)-5-oxo-D-prolinate as clear oil, R$_f$ 0.30 (hexanes-EtOAc 1:4). $^1$H NMR (400 MHz, CDCl$_3$) δ 7.36 (m, 5H, Ph), 5.19 (d, 1H, 12.0 Hz, CH$_2$Ph), 5.15 (d, 1H, 12.0 Hz, OCH$_2$Ph), 4.33 (m, 1H, CH—COOBn), 4.11 (m, 1H, cyclohexyl CH—CO), 3.62 (m, 1H, CH$_2$—N), 3.37 (m, 1H, CH$_2$—N), 2.89 (m, 1H, chain CH$_2$—CO), 2.66 (m, 1H, chain CH$_2$—CO), 2.43 (m, 1H, lactam ring CH$_2$—CO), 2.30 (m, 1H, lactam ring CH$_2$—CO), 2.27 (m, 1H, lactam ring H3) 2.02 (m, 1H, lactam ring H3), 1.85-1.55 (m, 5H, cyclohexyl), 1.30-1.15 (m, 5H, cyclohexyl). $^{13}$C NMR (100 MHz, CDCl3) δ 211.9 (CO—C$_6$H$_{11}$), 175.0 (—CO—

N), 171.7 (COOBn), 135.0 (ipso-C Ph), 128.5, 128.2 (o-C, m-C Ph), 128.4 (p-C Ph), 67.5 (OCH$_2$-Ph), 61.7 (CH—COOBn), 51.2 (cyclohexyl CH—CO), 39.2 (chain CH$_2$CO), 38.2 (CH$_2$—N), 30.1 (lactam ring CH$_2$—CO), 29.0, 26.5, 26.3 (cyclohexyl), 24.1 (lactam ring C3).

Intermediate 1.5 and 1.6: benzyl 1-[(3R)-3-cyclohexyl-3-hydroxypropyl]-5-oxo-D-prolinate and benzyl 1-[(3S)-3-cyclohexyl-3-hydroxypropyl]-5-oxo-D-prolinate To the stirring solution of benzyl 1-(3-cyclohexyl-3-oxopropyl)-5-oxo-D-prolinate (24.5 mmol, 8.80 g) in 100 ml MeOH and 20 ml H$_2$O at 0° C. cerium (III) chloride heptahydrate (25 mmol, 9.32 g) was added. To the resulting solution sodium borohydride (25 mmol, 0.95 g) was added quickly in small portions and the mixture was stirred at 0° C. After 15 min. the reaction was stopped by addition of a few ml of acetone and concentrated under vacuum giving 8.98 g of crude oil that contain a mixture of the 2 diastereoisomers. The mixture was separated on 300 g of silica gel, eluent hexanes-EtOAc from 100:0 to 0:100, to give:

Intermediate 1.5 (1.87 g, 21%), clear oil, Rf=0.32 (EtOAc). $^1$H NMR (400 MHz, CDCl$_3$) δ 7.35 (m, 5H, Ph), 5.20 (d, 1H, 12.0 Hz, CH$_2$Ph), 5.18 (d, 1H, 12.0 Hz, OCH$_2$Ph), 4.20 (m, 1H, CH—COOBn), 3.94 (m, 1H, CH$_2$—N), 3.13 (m, 1H, CH—OH), 2.93 (m, 1H, CH$_2$—N), 2.51 (m, 1H, lactam ring CH$_2$—CO), 2.40 (m, 1H, lactam ring CH$_2$—CO), 2.33 (m, 1H, lactam ring H3) 2.09 (m, 1H, lactam ring H3), 1.85 (m, 1H, cyclohexyl) 1.76-1.55 (m, 4H, cyclohexyl), 1.58 (m, 1H, CH$_2$—CHOH), 1.44 (m, 1H, CH$_2$—CHOH), 1.29 (m, 1H, cyclohexyl CH—CO), 1.30-0.9 (m, 5H, cyclohexyl). $^{13}$C NMR (100 MHz, CDCl$_3$) δ 175.9 (—CO—N), 171.1 (COOBn), 134.8 (ipso-C Ph), 128.6, 128.2 (o-C, m-C, p-C Ph), 72.1 (CH—OH), 67.7 (OCH$_2$-Ph), 60.1 (CH—COOBn), 44.0 (cyclohexyl CH—CHOH), 39.2 (CH$_2$—N), 32.0 (CH$_2$CHOH), 30.0 (lactam ring CH$_2$—CO), 29.8, 29.2, 27.2, 27.0, 26.9 (cyclohexyl), 23.7 (lactam ring C3).

Intermediate 1.6 (2.13 g, 24%) was obtained as a clear oil, Rf=0.25 (EtOAc); $^1$H NMR (400 MHz, CDCl$_3$) δ 7.33 (m, 5H, Ph), 5.18 (d, 1H, 12.0 Hz, CH$_2$Ph), 5.11 (d, 1H, 12.0 Hz, OCH$_2$Ph), 4.16 (m, 1H, CH—COOBn), 3.58 (m, 1H, CH$_2$—N), 2.29 (m, 1H, CH$_2$—N), 3.23 (m, 1H, CH—OH), 2.54 (m, 1H, lactam ring CH$_2$—CO), 2.34 (m, 1H, lactam ring CH$_2$—CO), 2.29 (m, 1H, lactam ring H3) 2.04 (m, 1H, lactam ring H3), 1.8 (br.t, 1H, cyclohexyl) 1.72-1.5 (m, 4H, cyclohexyl), 1.56 (m, 1H, CH$_2$—CHOH), 1.36 (m, 1H, CH$_2$—CHOH), 1.25 (m, 1H, cyclohexyl CH—CO), 1.25-0.9 (m, 5H, cyclohexyl). $^{13}$C NMR (100 MHz, CDCl$_3$) δ 176.2 (—CO—N), 171.6 (COOBn), 134.8 (ipso-C Ph), 128.6, 128.2 (o-C, m-C, p-C Ph), 72.4 (CH—OH), 67.7 (OCH$_2$-Ph), 60.1 (CH—COOBn), 44.0 (cyclohexyl CH—CHOH), 41.1 (CH$_2$—N), 32.7 (CH$_2$CHOH), 30.2 (lactam ring CH$_2$—CO), 29.7, 29.0, 27.2, 27.0, 26.9 (cyclohexyl), 24.2 (lactam ring C3).

Intermediate 1.7: benzyl 1-((3R)-3-{[tert-butyl(dimethyl)silyl]oxy}-3-cyclohexylpropyl)-5-oxo-D-prolinate To the stirring solution of intermediate 1.5 (5.6 mmol, 2.00 g) in 20 ml anhydrous DMF, cooled to 0° C., triethylamine (20 mmol, 2.8 ml) was added by syringe under nitrogen atmosphere followed by tert-butyldimethylsilyltrifluoromethanesulfonate (8.4 mmol, 1.46 ml). The solution was stirred overnight, concentrated under vacuum, diluted with 100 ml water, extracted with EtOAc (3×20 ml), extracts dried over MgSO$_4$, and concentrated to give 2.65 g (100%) of the title compound as clear oil that was used in the next step without further purification.

Intermediate 1.8 (5R)-1-((3R)-3-{[tert-butyl(dimethyl)silyl]oxy}-3-cyclohexylpropyl)-5-(hydroxymethyl)pyrrolidin-2-one To the stirring solution of intermediate 1.7 (5.6 mmol, 2.65 g) in MeOH (200 ml) sodium borohydride (7.1 mmol, 270 mg) was added in three portions over 8 h and the reaction mixture was stirred overnight, then concentrated in vacuo. Purification on 200 g silica gel, eluent hexanes-EtOAc from 80:20 to 0:100 resulted in 0.79 g (39%, or 44% on reacted ester) of the title product as white waxy solid. R$_f$ 0.20 (EtOAc); $^1$H NMR (400 MHz, CDCl$_3$) δ 3.78 (dd, 1H, 11.4 Hz, 3.7 Hz, CH$_2$OH), 3.70 (br.td, 1H, ~8 Hz, ~4 Hz, CHCH$_2$OH), 3.65 (m, 1H, CH$_2$—N), 3.62 (dd, 1H, 11.4 Hz, 3.3 Hz, CH$_2$OH), 3.49 (br.quint, ~4 Hz, CH-OTBS), 3.03 (ddd, 1H, 13.6 Hz, 11.0 Hz, 4.8 Hz, CH$_2$—N), 2.46 (ddd, 1H, 17 Hz, 10 Hz, 7.3 Hz, lactam ring CH$_2$—CO), 2.31 (ddd, 1H, 17 Hz, 10 Hz, 5.5 Hz, lactam ring CH$_2$—CO), 2.08 (m, 1H, lactam ring H3) 1.97 (m, 1H, lactam ring H3), 1.8-1.6 (m, 5H, cyclohexyl), 1.66 (m, 1H, CH$_2$—CHOTBS), 1.55 (m, 1H, CH$_2$—CHOTBS), 1.38 (br.tq, 1H, ~12 Hz, ~4 Hz, cyclohexyl CH—CHOTBS), 1.2-0.9 (m, 5H, cyclohexyl). $^{13}$C NMR (100 MHz, CDCl$_3$) δ 175.1 (—CO—N), 75.0 (CH-OTBS), 63.0 (CH$_2$OH), 59.2 (CH—CH$_2$OH), 44.5 (cyclohexyl CH—CHOTBS), 38.7 (CH$_2$—N), 31.2 (lactam ring CH$_2$—CO), 31.0 (CH$_2$—CHOTBS), 29.5, 28.4, 27.4, 27.2, 27.1 (cyclohexyl), 26.6 (C(CH$_3$)$_3$), 21.9 (lactam ring C3), 18.9 (Si—CMe$_3$), −3.5 (Si—CH$_3$)

Intermediate 1.9: (2R)-1-((3R)-3-{[tert-butyl(dimethyl)silyl]oxy}-3-cyclohexylpropyl)-5-oxopyrrolidine-2-carbaldehyde In a dried, nitrogen flushed 25-ml flask, oxalyl chloride (0.36 mmol, 31 μl) was added into 5 ml dichloromethane at −78° C. under nitrogen, followed by DMSO (0.45 mmol, 35 μl). After 10 min, the intermediate 1.8 (0.28 mmol, 103 mg) in 2 ml CH$_2$Cl$_2$ was added through a septum completing the transfer with 2-3 ml CH$_2$Cl$_2$. The mixture was stirred at −78° C. for 1.2 h then triethylamine (1.40 mmol, 194 μl) was added, and stirred for 15 min. TLC control of the reaction was difficult due to a by-product formation with R$_f$ 0.20, identical to that of the starting alcohol. The CO$_2$-acetone bath was substituted by an ice bath, stirring continued for another 5 min, and the reaction was quenched by 10 ml saturated aqueous NH$_4$Cl. Layers were separated, the organic one washed with brine (5 ml), dried over MgSO4, and concentrated to give 120 mg of title compound as clear oil, R$_f$ 0.39 (EtOAc) that was used without further purification in the next step.

Intermediate 1.10: methyl 4-{3-[(2R)-1-((3R)-3-{[tert-butyl(dimethyl)silyl]oxy}-3-cyclohexylpropyl)-5-oxopyrrolidin-2-yl]prop-2-enyl}benzoate To a stirred suspension of intermediate 1.1 (1.12 mmol, 550 mg) in 10 ml THF potassium tert-butoxide solution (1M in THF, 2.24 mmol, 2.24 ml) was added dropwise at 0° C. under nitrogen. After 15 min the solution of intermediate 1.9 (0.28 mmol) in 2 ml THF was added, completing the transfer with another 3 ml THF. The mixture was stirred at 0° C. for 4 h until reaction was complete (TLC control). Then 20 ml EtOAc was added, the reaction was cooled by ice bath, acidified with aqueous hydrochloric acid (1M, 2.24 mmol, 2.24 ml), and stirred for 15 min. At this point the grey suspension turned into a yellow solution with little of white precipitate. The organic phase was decanted, washed with EtOAc (10 ml), and decanted again. The organic phase was dried over MgSO$_4$ and concentrated.

The free acid proved to be difficult to separate from triphenyl phosphine oxide and other impurities, and the crude reaction mixture was converted to methyl ester to simplify separation (see below).

To a solution of the above mixture in 10 ml dichloromethane and 5 ml methanol was added trimethylsilyldiazomethane (2M in hexanes, 0.42 mmol, 0.24 ml) and stirred overnight at rt. The reaction was concentrated and purified on silica gel to give 61 mg (43% over 3 steps) of the title compound as clear oil.

Intermediate 1.11: methyl 4-(3-{(2S)-1-[(3R)-3-cyclohexyl-3-hydroxypropyl]-5-oxopyrrolidin-2-yl}propyl)benzoate To a solution of intermediate 1.10 (0.12 mmol, 61 mg) in 7 ml MeOH was added palladium on activated carbon (10% Pd, 0.019 mmol, 20 mg) and 1 drop (~0.05 ml) of concentrated hydrochloric acid. The mixture was stirred overnight under balloon filled with H$_2$. Then the mixture was filtered from the catalyst and concentrated to give 41 mg of clear oil. Purification on 4 g silica gel, eluent hexanes-EtOAc from 90:10 to 0:100 afforded 32.4 mg (66%) of title compound as clear oil. $^1$H NMR (400 MHz, CDCl$_3$) δ 7.95 (d, 2H, 8.0 Hz, o-H Ar), 7.22 (d, 2H, 8.0 Hz, m-H Ar), 3.88 (s, 3H, COOMe), 3.85 (ddd, 1H, 14.3 Hz, 11.7 Hz, 5.6 Hz, N—CH2), 3.51 (dm, 1H, ~8 Hz, lactam ring C$\underline{H}$—CH$_2$), 3.05 (ddd, 1H, 11.0 Hz, 5.8 Hz, 2.2 Hz, C$\underline{H}$OH), 2.88 (ddd, 1H, 14.3 Hz, 4.8 Hz, 3.6 Hz, N—CH$_2$), 2.69 (m, 2H, CH$_2$—Ar), 2.36 (m, 2H, lactam ring CH$_2$—CO), 2.12 (m, 1H, lactam ring H3), 1.85 (br.d, 1H, 12 Hz cyclohexyl), 1.75-1.50 (m, 8H, cyclohexyl, alkyl), 1.37 (m, 1H, cyclohexyl C$\underline{H}$—CHOH), 1.3-0.9 (m, 8H, cyclohexyl, alkyl). $^{13}$C NMR (100 MHz, CDCl$_3$) δ 175.6 (CO—N), 166.6 (COOMe), 146.8 (Cl Ar), 129.7, 128.2 (o-C, m-C Ar), 127.9 (p-C Ar), 71.7 (CHOH), 57.2 (lactam ring N—CH), 52.5 (OCH$_3$), 43.9 (cyclohexyl C$\underline{H}$—CHOH), 36.8 (CH$_2$—N), 36.3 (CH$_2$Ar), 32.7 (N—CH—C$\underline{H}$2), 31.8 (C$\underline{H}$$_2$—CHOH), 30.6 (lactam ring C$\underline{H}$$_2$—CO), 29.9, 29.4, 27.2, 27.0, 26.9 (cyclohexyl), 26.6 (C$\underline{H}$$_2$—CH$_2$—Ar), 24.8 (lactam ring C3).

4-(3-(2S)-1-[(3R)-3-cyclohexyl-3-hydroxypropyl]-5-oxotetrahydro-1H-2-pyrrolylpropyl)benzoic acid (Example 1)

To a solution of intermediate 1.11 (0.080 mmol, 32.4 mg) in 2 ml MeOH and 1 ml H$_2$O was added a solution of NaOH (10M in H$_2$O, 0.80 mmol, 80 μl), and the solution was stirred overnight. TLC showed complete consumption of the ester. The reaction was concentrated under vacuum, diluted with 5 ml water, and acidified with hydrochloric acid (1M in H$_2$O, 0.80 mmol, 0.80 ml)—a white oily solid precipitation observed. The mixture was extracted with EtOAc (3×3 ml), dried with MgSO$_4$, filtered, and concentrated to give 31 mg (100%) of title compound as white waxy solid. Na-salt of the acid was prepared by titration of the solution of the product in 1 ml MeOH, diluted by 1 ml H$_2$O, with 1M solution of NaOH (90 μl) at intensive shaking until the solids were dissolved. The resulting solution was lyophilized over 2 days giving 33 mg (100%) of bulky white solid. $^1$H NMR (400 MHz, CD$_3$OD, Na-salt) δ 7.86 (d, 2H, 8.0 Hz, o-H Ar), 7.19 (d, 2H, 8.0 Hz, m-H Ar), 3.75 (m, 1H, N—CH2), 3.55 (m, 1H, lactam ring C$\underline{H}$—CH$_2$), 3.12 (m, 2H, C$\underline{H}$OH, N—CH$_2$), 2.70 (m, 2H, CH$_2$—Ar), 2.33 (m, 2H, lactam ring CH$_2$—CO), 2.12 (m, 1H, lactam ring H3), 1.85-1.55 (m, 9H, cyclohexyl, alkyl), 1.50-0.9 (m, 9H, cyclohexyl, alkyl). MS (m/z): 388 (M+H$^+$).

Example 2

Synthesis of 4-(3-(2S)-1-[(3S)-3-cyclohexyl-3-hydroxypropyl]-5-oxotetrahydro-1H-2-pyrrolylpropyl) benzoic acid

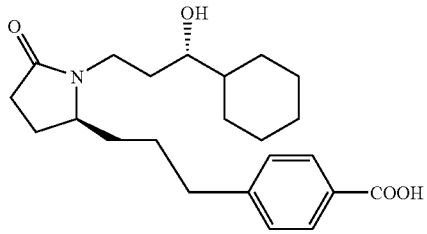

Intermediate 2.1: benzyl 1-((3S)-3-{[tert-butyl(dimethyl)silyl]oxy}-3-cyclohexylpropyl)-5-oxo-D-prolinate The 3S isomer was obtained according to the procedure of intermediate 1.7 from intermediate 1.6 (5.9 mmol, 2.13 g) resulting in 2.80 g (100%) of clear oil that was used without purification.

Intermediate 2.2: (5R)-1-((3S)-3-{[tert-butyl(dimethyl)silyl]oxy}-3-cyclohexylpropyl)-5-(hydroxymethyl)pyrrolidin-2-one The 3S isomer was prepared according to the procedure of intermediate 1.8 from intermediate 2.1 (5.9 mmol, 2.80 g) resulting in 0.93 g (43%, or 50% on reacted ester), R$_f$ 0.18 (EtOAc). $^1$H NMR (400 MHz, CDCl$_3$) δ 3.77 (dd, 1H, 11.0 Hz, 3.7 Hz, C$\underline{H}$$_2$OH), 3.67 (m, 1H, C$\underline{H}$CH$_2$OH), 3.64 (dd, 1H, 11.4 Hz, 3.7 Hz, C$\underline{H}$$_2$OH), 3.55 (ddd, 13.6 Hz, 11.4 Hz, 5.5 Hz, 1H, CH$_2$—N), 3.47 (dt, 6.6 Hz, 4.8 Hz, CH—OTBS), 3.03 (ddd, 1H, 13.6 Hz, 1.0 Hz, 4.8 Hz, CH$_2$—N), 2.46 (ddd, 1H, 17 Hz, 9.9 Hz, 7.0 Hz, lactam ring CH$_2$—CO), 2.31 (ddd, 1H, 17 Hz, 10 Hz, 5.5 Hz, lactam ring CH$_2$—CO), 2.10 (m, 1H, lactam ring H3) 1.93 (m, 1H, lactam ring H3), 1.73-1.55 (m, 7H, cyclohexyl, C$\underline{H}$$_2$—CHOTBS), 1.39 (tm, 1H, ~11 Hz, cyclohexyl C$\underline{H}$—CHOTBS), 1.2-0.9 (m, 5H, cyclohexyl). $^{13}$C NMR (100 MHz, CDCl$_3$) δ 175.2 (—CO—N), 74.9 (CH—OTBS), 63.1 (CH$_2$OH), 59.9 (C$\underline{H}$—CH$_2$OH), 43.3 (cyclohexyl C$\underline{H}$—CHOTBS), 38.2 (CH$_2$—N), 31.8 (C$\underline{H}$$_2$CHOTBS), 31.1 (lactam ring C$\underline{H}$$_2$—CO), 29.3, 29.1, 27.3, 27.1, 27.1 (cyclohexyl), 26.6 (C(C$\underline{H}$$_3$)$_3$), 21.9 (lactam ring C3), 18.8 (Si—CMe$_3$), −3.3, −3.5 (Si—CH$_3$). MS (m/z): 392 (M+Na$^+$).

Intermediate 2.3: (2R)-1-((3S)-3-{[tert-butyl(dimethyl)silyl]oxy}-3-cyclohexylpropyl)-5-oxopyrrolidine-2-carbaldehyde The 3S isomer was prepared according to the procedure of intermediate 1.9 from intermediate 2.2 (0.30 mmol, 125 mg) in quantitative crude yield as clear oil, R$_f$ 0.43 (EtOAc), that was pure by TLC (unlike the 3R isomer) and was used in the next step without purification.

Intermediate 2.4: methyl 4-{3-[(2R)-1-((3S)-3-{[tert-butyl(dimethyl)silyl]oxy}-3-cyclohexylpropyl)-5-oxopyrrolidin-2-yl]prop-2-enyl}benzoate The 3S isomer was prepared according to the procedure of intermediate 1.10 from intermediate 2.3 (0.33 mmol) yielding 87.1 mg (51% over 3 steps) of the product.

Intermediate 2.5: methyl 4-(3-{(2R)-1-[(3S)-3-cyclohexyl-3-hydroxypropyl]-5-oxopyrrolidin-2-yl}propyl)benzoate The 3S isomer was prepared according to the procedure of intermediate 1.11 from intermediate 2.4 (0.17 mmol, 87 mg) afforded 53.7 mg (79%) of the product. $^1$H NMR (400 MHz, CDCl$_3$) δ 7.93 (d, 2H, 8.0 Hz, o-H Ar), 7.20 (d, 2H, 8.0 Hz, m-H Ar), 3.87 (s, 3H, COOMe), 3.59 (m, 1H, N—CH2), 3.54 (m, 1H, lactam ring N—C$\underline{H}$—CH$_2$), 3.18 (ddd, 1H, 10.6 Hz, 6.2 Hz, 2.6 Hz, C$\underline{H}$OH), 2.88 (ddd, 1H, 14 Hz, 5 Hz, 4 Hz, N—CH$_2$), 2.68 (m, 2H, CH$_2$—Ar), 2.37 (m, 1H, lactam ring CH$_2$—CO), 2.30 (m, 1H, lactam ring CH$_2$—CO), 2.13 (m, 1H, lactam ring H3), 1.85-0.9 (m, 18H, cyclohexyl, alkyl). $^{13}$C NMR (100 MHz, CDCl$_3$) δ 176.2 (CO—N), 166.5 (COOMe), 146.8 (Cl Ar), 129.6, 128.2 (o-C, m-C Ar), 127.9 (p-C Ar), 72.3 (CHOH), 60.9 (lactam ring N—CH), 52.5 (OCH$_3$), 44.0 (cyclohexyl C$\underline{H}$—CHOH), 39.8 (CH$_2$—N), 36.4 (CH$_2$Ar), 34.7 (N—CH—C$\underline{H}$2), 34.1 (C$\underline{H}_2$—CHOH), 30.9 (lactam ring C$\underline{H}_2$—CO), 29.8, 29.3, 27.2, 27.0, 26.9 (cyclohexyl), 26.8 (C$\underline{H}_2$—CH$_2$—Ar), 25.2 (lactam ring C3).

4-(3-{(2S)-1-[(3S)-3-cyclohexyl-3-hydroxypropyl]-5-oxopyrrolidin-2-yl}propyl)benzoic acid (Example 2)

The 3S isomer was prepared according to the procedure of intermediate 1.11 from intermediate 2.5. The crude acid was purified on 0.8 g silica gel, eluent EtOAc-MeOH from 100:0 to 60:40 yielding 35.2 mg (68%) of pure acid. Subsequent preparation of the Na salt resulted in 34.9 mg (94%) of white solid. $^1$H NMR (400 MHz, CDCl$_3$) δ 8.01 (d, 2H, 8.4 Hz, o-H Ar), 7.27 (d, 2H, 8.0 Hz, m-H Ar), 3.88 (m, 1H, N—CH2), 3.54 (m, 1H, lactam ring C$\underline{H}$—CH$_2$), 3.06 (m, 1H, C$\underline{H}$OH), 2.90 (m, 1H, N—CH$_2$), 2.73 (m, 2H, CH$_2$—Ar), 2.38 (m, 2H, lactam ring CH$_2$—CO), 2.13 (m, 1H, lactam ring H3), 1.85 (br.d, 1H, 12 Hz cyclohexyl), 1.80-1.55 (m, 8H, cyclohexyl, alkyl), 1.45-0.9 (m, 9H, cyclohexyl, alkyl). MS (m/z): 388 (M+H$^+$, 45).

Example 3

Synthesis of 7-{(2S)-1-[(3R)-3-cyclohexyl-3-hydroxypropyl]-5-oxopyrrolidin-2-yl}heptanoic acid

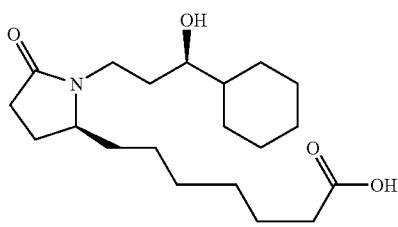

Intermediate 3.1:
6-Carboxyhexyl(triphenyl)phosphonium bromide

A solution of 6-bromohexanoic acid (18 mmol, 3.50 g) and triphenylphosphine (18 mmol, 4.71 g) in acetonitrile (18 mL) was refluxed for 18 h. The reaction mixture was then cooled down, the off-white solid formed filtered. Flash chromatography over silica gel (EtOAc then MeOH) afforded the product as a white solid (1.08 g, 86%).

7-{(2S)-1-[(3R)-3-cyclohexyl-3-hydroxypropyl]-5-oxopyrrolidin-2-yl}heptanoic acid (Example 3)

The compound was prepared from Intermediate 3.1 and Intermediate 1.9 according to procedure for Example 1. $^1$H NMR (400 MHz, CD$_3$OD, Na-salt) δ 3.6-3.75 (m, 2H), 3.20-3.30 (m, 1H), 3.05-3.15 (m, 1H), 2.20-2.40 (m, 4H), 2.10-2.20 (m, 1H), 1.55-1.90 (m, 10H), 0.90-1.45 (m, 14H). MS (m/z): 354.1 (M+H$^+$).

Example 4

Synthesis of 7-{(2S)-1-[(3R)-3-cyclohexyl-3-hydroxypropyl]-5-oxopyrrolidin-2-yl}heptanoic acid

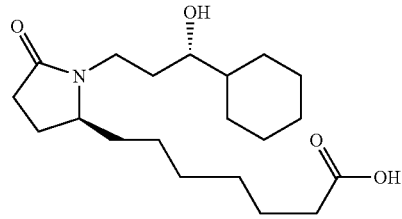

The compound was obtained from Intermediate 3.1 and Intermediate 2.3 according to procedure of Example 2. $^1$H NMR (400 MHz, CD$_3$OD, Na-salt) δ 3.65-3.75 (m, 1H), 3.45-3.55 (m, 1H) 3.10-3.30 (m, 2H), 2.20-2.40 (m, 4H), 2.10-2.20 (m, 1H), 1.55-1.90 (m, 10H), 0.90-1.45 (m, 14H). MS (m/z): 354.1 (M+H$^+$).

Example 5

Assays For Determining Biological Activity of the Compounds of the Invention

The compounds of the present invention can be tested using a variety of biological assays in order to determine the prostanoid agonist (or even antagonist) activity in vitro and in vivo and to assess the selectivity of the compounds with respect to a given prostanoid receptor. The compounds of the present invention are preferably specific for the DP$_1$ receptor. Both the DP$_1$ and the DP$_2$ receptors are well known to those of skill in the art and have been described e.g., in U.S. Pat. No. 6,395,499; Hawcroft et al., (Cancer Lett. 2004 Jul. 8; 210(1): 81-4, describing expression of prostaglandin D2 receptors DP$_1$ and DP$_2$ by human colorectal cancer cells); Hammad et al., (J Immunol. 2003 Oct. 15; 171(8):3936-40; describing activation by prostaglandin D2 of DP$_1$ receptor in airway dendritic cell migration and function); Monneret et al., (Blood. 2001 Sep. 15; 98(6):1942-8), describing DP$_2$ receptors in human eosinophils). Other prostaglandin receptors that may be used to test the activity of the present compounds include EP$_1$, EP$_2$, EP$_3$, EP$_4$, FP, IP and TP

5.1 Stable Expression of Prostanoid Receptors in Cell Line

Prostanoid receptor cDNAs corresponding to full length coding sequences are well known to those of skill in the art and may be subcloned into the appropriate sites of mammalian expression vectors and transfected into any host cell commonly used for stable transfection. Such cells include e.g., VERO cells, HeLa cells, Chinese hamster ovary (CHO) cell lines, COS cells (such as COS-7), WI 38, BHK, HepG2, 3T3, RIN, MDCK, A549, PC 12, K562 and HEK 293 cells. A preferred cell line for use in such embodiments is the human embryonic kidney cells (HEK-293) that have been transfected with and express the EBNA-1 protein. Upon transfection, the HEK 293(ebna) cells expressing the individual cDNAs are grown under selection and individual colonies are isolated after 2-3 weeks of growth using the cloning ring method and subsequently expanded into clonal cell lines.

5.2 Prostanoid Receptor Binding Assays

HEK 293(ebna) cells or other cells stably transfected with the appropriate receptor are maintained in culture, harvested and membranes are prepared by differential centrifugation, following lysis of the cells in the presence of protease inhibitors, for use in receptor binding assays.

Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand for the given receptor. The reaction is initiated by addition of membrane protein. Typically, the ligands are added in a solvent such as dimethylsulfoxide which is kept constant at 1% (v/v) in all incubations. Non-specific binding is determined in the presence of 1 µM of the corresponding non-radioactive prostanoid. Incubations are conducted for 60 min at room temperature or 30° C. and terminated by rapid filtration. Specific binding is calculated by subtracting non-specific binding from total binding. The residual specific binding at each ligand concentration is calculated and expressed as a function of ligand concentration in order to construct sigmoidal concentration-response curves for determination of ligand affinity.

In another protocol, compounds of the invention are tested in $DP_1$ receptor binding assay of the following protocol. A mixture containing 20 µg of $DP_1$ receptor membranes, 0.5 mg of wheat germ agglutinin coated PVT-SPA beads, plus or minus a test compound of the invention (25 µl per well) or 10 µM of cold PGE2 at 1% DMSO and 20 nM radiolabeled ligand for the receptor (e.g., tritiated-PGE2) in assay buffer containing 25 mM MES, 10 mM $MgCl_2$, 1 mM EDTA, pH 6.0 are incubated in Corning 3600 plates on a plate shaker for 2 hrs at room temperature. Binding of the radiolabeled ligand binding is evaluated by counting the plates on the top count using the 3H SPA dpm2 program. % Binding and Ki value for inhibitors are calculated based on the one site competition parameter using the Graphpad® prism program. Such an assay may be modified by employing the different receptors and their specific ligands to assess the activity of the compounds of the present invention against such receptors. Using such an assay, the $DP_1$ Ki values for a number of exemplary compounds of the present invention were calculated and are shown in Table 1. As can be seen from the Table below, a comparison of the Ki values against $DP_1$ as compared to Ki values of these compounds against $DP_2$, shows that exemplary agonists of the present invention are specific for $DP_1$ as compared to these other prostaglandin receptors ($K_i$ values for h-$EP_2$, h-$EP_3$ and h-$EP_4$ of >10000 nM).

TABLE 1

| | Inhibition of $DP_1$ | | |
|---|---|---|---|
| Example # | h-$DP_1$ $K_i$ (nM) | h-$DP_1$ $EC_{50}$ (nM) | h-$DP_2$ $K_i$ (nM) n = 2 |
| PGD2 | 4.1 | 0.3 | |
| BW245C | | 0.031 | |
| 1 | 2.4 | 0.00072 | >10000 |
| 2 | 10.5 | 0.71 | >10000 |
| 3 | 1.8 | 0.037 | >10000 |
| 4 | 47.2 | 1.38 | >10000 |

5.3 Whole Cell Second Messenger Assays

Whole cell second messenger assays measuring stimulation ($EP_2$, $EP_4$, $DP_1$, $DP_2$ and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 µM RO-20174 (phosphodiesterase type IV inhibitor, available from Biomol) and, in the case of the $EP_3$ inhibition assay only, 15 µM forskolin to stimulate cAMP production.

Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations.

For agonists, second messenger responses are expressed as a function of ligand concentration and both EC50 values and the maximum response as compared to a prostanoid standard are calculated. For antagonists, the ability of a ligand to inhibit an agonist response is determined by Schild analysis and both KB and slope values are calculated.

In another exemplary protocol, HEK293-EBNA cells transfected with the appropriate receptors are seeded in 96 well opaque plate (Costar #3917) at $4\times10^4$ cells per well in 100 µl of culture medium (D-MEM/F12 supplemented with 10% FBS, 2 nM L-glutamine, and 250 µg/ml of hygromycin; all from GibcoBRL) and incubated at 37° C. After overnight incubation, the medium was removed from each well and replaced with 45 µl of assay medium consisted of phenol red free D-MEM/F-12, 0.1% BSA (GibcoBRL) and 0.1 mM 3 isobutyl-1-methyl-xanthine (Sigma). After 15 minutes of incubation at 37° C., 16-16-dimethyl PGE-2 or compounds at desired concentrations in 20 µl of assay medium were added to cells and further incubated at 37° C. for 1 hour. Total cAMP (intra- and extracellular) was measured by using a cAMP-screen ELISA System (Tropix #CS1000).

5.4 In Vivo Ovulation Assay

Ovulation triggering activity of compounds of the invention are tested in a mature mouse ovulation induction model. Mature 10-week-old CD-mice are used. Reagents are prepared as follows: PMSG (pregnant mare serum gonadotropin) (Calbiochem, cat #367222) and hCG (Serono) are diluted in PBS. PGE2 (Cayman, Ann Arbor Mich.) is dissolved in ethanol and diluted with 0.154 M $NaHCO_2$ Buffer (pH 8.0) to final concentration of ethanol of less than 3 percent. A test compound (based on solubility) is pre-dissolved in ethanol, DMSO or other reagents. Test compound is then diluted with saline or other diluents such as PBS or NP3S (5% N-methyl-pyrrolidinone/30% PEG-400/25% PEG-200/20% Propylene Glycol in saline). PMSG serves to stimulate follicle growth and maturation.

Mature follicles will ovulate when an ovulation triggering dose of hCG or an hCG replacement is administered. The following test protocol was employed for the test animals (typically 5 animals per test group).

Day 1: Inject 5IU PMSG in 200 UL PBS (i.p. 15:00 PM)
Day 2: No administration
Day 3: Inject an ovulation triggering dose of hCG (i.p.) or hCG replacement (PGE2 or compound of the invention, s.c., i.v. or oral route), 15:00 PM
Day 4: Eighteen hours after injections of ovulation triggers, animals were sacrificed by $CO_2$ asphyxiation and abdominal cavities were opened using fine scissors and forceps. Uterus, oviducts and ovaries were collected and placed in pre-labeled dishes containing phosphate buffered saline (PBS). The collected tissues were transferred to the laboratory and intact oviduct carefully dissected out from uterus and ovary under the dissection microscope. The dissected oviducts were placed on the glass microscopic slide and covered with another slide. Two slides were taped on two edges. The numbers of ovulated ova in the oviducts were counted using upright microscope with 4× objective and recorded.

For evaluating the oral activity of this compound, two experiments were conducted, the first experiment was conducted with non-fasted animals and the second experiment was conducted in 24 h fasted animals (water provided). The compounds of the invention, according to their solubility are pre-dissolved in ethanol, DMSO or other reagents. The compounds of the invention are then diluted with saline or other diluents such as PBS or NP3S before oral administration.

Compounds of the invention may be tested in the in vivo ovulation induction model as described above in order to assess the ability of those compounds to trigger ovulation via subcutaneous (sc), oral (po) and intravenous (iv) routes of administration. Test groups may be assessed as follows:

| Groups | Priming | Treatments |
| --- | --- | --- |
| Group 1 | 5IU PMSG | Control Vehicle |
| Group 2 | 5IU PMSG | HCG (0.12 mg/kg i.p.) |
| Group 3 | 5IU PMSG | PGE2 (13.5 mg/kg) |
| Group 4 | 5IU PMSG | Test compound (10 mg/kg) |
| Group 5 | 5IU PMSG | Test compound (30 mg/kg) |
| Group 6 | 5IU PMSG | Test compound (90 mg/kg) |

Using test groups as set forth above, it is possible to determine the number of ova obtained from each group and thereby assess the effects of the compounds on stimulation of ovulation.

Agonists of $DP_1$ are selected using the assays described above on the basis of their Ki and/or $EC_{50}$ values.

The compounds of the invention are then tested in the in vivo ovulation induction model as described above in order to calculated the $ED_{50}$ for subcutaneous (s. c.) and oral (po) routes of administration. Data also may be obtained for reference compounds (sulprostone and butaprost) that do not fulfill the selection criteria for $DP_1$ agonists in order to provide a comparison of activity.

In exemplary embodiments, oral activity in the in vivo model of ovulation induction is evaluated for other compounds of the invention at the single dose of 20 mg/kg.

It is desirable that the compounds of the invention are able to stimulate ovulation induction in mature mice in at least one of the routes of administration. Preferably, the compounds are able to stimulate ovulation in all three routes of administration (sc, iv, and po).

5.5. In Vivo Inhibition of Guinea Pig Broncho-Constriction

Guinea pig pulmonary-cholinergic in vivo model is generally used to test the materials for the treatments of asthma in human (Fleisch at al. 1985, K. Pharmacol. Exp. Ther. 233: 148-157). Compounds of the invention are tested in this model.

Groups of 3 Duncan Hartley derived male or female guinea pigs weighing 250±50 g are anesthetized with pentobarbital sodium (50 mg/kg i.p., plus an additional 15 mg/kg i.p. if required) and succinylcholine chloride (2 mg/animal i. p.) is subsequently administered to prevent spontaneous respiration. Body temperature is maintained at 37° C. to 38° C.

The trachea is cannulated and the guinea pig is ventilated with a Harvard rodent respirator in a closed system. Tracheal pressure is recorded through a side-arm of the cannula connected to a P23ID Statham transducer. Respiratory rate is set at 50 strokes/minute with a stroke volume (approximately 1 ml/100 g) sufficient to produce a baseline tracheal pressure of 6 $cmH_2O$. Mean arterial pressure (BP) is monitored from a cannulated carotid artery, and heart rate (HR) is obtained from chest electrodes arranged for lead II. The jugular vein is cannulated for i. v. vehicle or drug administration in a volume of 1 ml/kg.

Cholinergic-induced bronchoconstrictor responses, reflected as increases in tracheal pressure (cm $H_2O$), are elicited by administration of methacholine hydrochloride (10 µg/kg base weight i. v.). In vehicle-treated control animals, methacholine-induced bronchoconstriction ranges from 70 to 90 percent of its own maximum response (about 40 to 65 percent of maximum possible bronchoconstriction obtained by tracheal occlusion).

Compounds of the invention are also tested via intratracheal (IT) route of administration. In this other experiment, a test compound of the invention, reference compound or vehicle is administered IT 10 (5 min for experiment 1 and 2) minutes before methacholine chloride (10 µg/kg i.v.) induced bronchoconstriction. Tracheal pressure (ITP), blood pressure and heart rate are measured immediately as indicated in the material and methods sections.

MED (medium effective dose) is measured. A 50 percent or greater ($\geq 50\%$) inhibition of the induced bronchoconstriction relative to vehicle treated control animals is considered significant.

Compounds of the invention are administered i.v. (10 mg/kg) 5 minutes before subministration of the methacoline hydrochloride challenge in 3 guinea pigs. A 50 percent or more ($\geq 50$) inhibition of the induced bronchoconstriction relative to vehicle treated control animals is considered significant.

Test compounds of the invention are injected i.v. to different concentrations from $3 \times 10^5$ mg/kg up to 0.3 mg/kg. From such studies, the concentration at which methacholine-induced bronchoconstriction (>50%) inhibitions are observed may readily be calculated and the in vivo effective dose ($ED_{50}$) determined. Preferably, although not necessarily, the compounds do not alter blood pressure or heart beat.

In these model studies the doses may be varied. For example the compound may be tested at 0.04, 0.4, 4.0 and 40 µg/guinea pig. Reference material e.g., salbutamol (40 µg/animal) and vehicle control were also may be tested.

Conducting the above studies demonstrates the ability of the compounds of the invention to produce dilation of bronchiolar muscles, which resulted in inhibition of methacholine-induced bronchomuscle constriction.

5.5. In Vivo Inhibition of LPS-Induced TNFα Release in Mice

The agonists of the invention may be useful as anti-inflammatory agents, whereby the agonists act as inhibitors of inflammation mediated through prostaglandin receptors, and especially through $DP_1$ receptor and/or the $DP_2$.

Endotoxins are the lipopolysaccharides (LPS) constituents of the outer membrane of Gram negative bacteria. Response to LPS has been shown to involve the activation of different cell populations and to lead to the expression of various inflammatory cytokines that include tumor necrosis factor-alpha (TNFα) and interferon gamma (IFN-γ).

The anti-inflammatory activity of compounds of the invention may be assessed after a LPS challenge using the following protocol:

Eight weeks old C3H/HEN mice (IFFA-CREDO, L'arbresle, France) receive an oral treatment with compounds of the invention at e.g., 6 different doses (0.001, 0.01, 0.1, 1 or 3 and 10 mg/kg in 0.5% CMC/0.25% tween-20). Six mice are used by group. Fifteen minutes later, endotoxins (O111: B4 Sigma, 0.3 mg/kg) are intraperitoneally injected. Heparinized whole blood is collected by decapitation. TNFα level is determined in plasma by ELISA (R & D Systems, Abdingdon, UK). Control animals receive 0.5% CMC/0.25% tween-20 (10 ml/kg) as vehicle. Data obtained from experiments are expressed as the mean ±SEM and analysed using one-way analysis of variance (ANOVA) followed by Dunnett's t-test.

The activity of the compounds of the invention is expressed as a percentage of inhibition of TNF release and the Inhibitory Dose at 50% of the maximum effect ($ID_{50}$) is calculated in mg/kg. Using such an experimental protocol, data are generated to show whether the compounds of the invention inhibit the release of TNF alpha in a LPS-challenge model.

The following additional assays also may be performed to determine the anti-inflammatory effects of the compounds of the invention. The compounds may be assessed for efficacy against: edema using a rat paw edema assay as described in e.g., Chan et al. (J. Pharmacol. Exp. Ther. 274: 1531-1537, 1995); LPS-induced pyrexia in conscious rats as described in e.g., Chan et al. (J. Pharmacol. Exp. Ther. 274: 1531-1537, 1995); LPS-induced pyrexia in conscious squirrel monkeys as described in e.g., Chan et al. (Eur. J. Pharmacol. 327: 221-225, 1997); acute inflammatory hyperalgesia induced by carrageenan in rats as described in e.g., Boyce et al. (Neuropharmacology 33: 1609-1611, 1994).

5.6 In Vivo Effect on Penile Corpus Cavernosum Tissue Relaxation

Penile erection is based on three main physiological events: an increase in the arterial blood flow, a relaxation of the expansive tissue of the corpora carvernosa and the corpus spongiosum, and an obstruction of the venous return by mechanicak compression of the veins caused by the expansive tissue.

PGE1 is used in the treatment of erectile dysfunction to relax smooth muscle and therefore to promote the development of erection. The administration of PGE1 is performed by local injection into the cavernous tissue of the penis. However, PGE1 has a low selectivity for prostanoid receptors and has irritant effects. Selective agonists of $EP_2$ and/or $EP_4$ have been developed for the treatment of erectile dysfunction (WO 9902164)

The effect of compounds of the invention on the relaxation of penile corpus cavernosal tissue strips may be assayed for example in an assay on human or rabbit tissue as described below:

Human tissue procurement. Cavernosal tissue is obtained from patients undergoing penile prosthesis implantation surgery for treatment of erectile dysfunction. In the operating room, biopsies of the corpora cavernosa are immediately placed in chilled (4° C.) physiologic salt solution and transported to the laboratory. Tissue strips, measuring approximately 3 mm×3 mm×10 mm, are cut and prepared for organ bath studies.

Rabbit tissue procurement. Adult male New Zealand White rabbits (4.5-5.0 kg) are sedated with ketamine (35 mg/kg) and xylazine (5 mg/kg) and euthanized with sodium pentobarbital (60 mg/kg body weight). Following exsanguination, the penis is excised and cleaned by removing the corpus spongiosum and urethra. Corpus cavernosum tissue strips are dissected away from the surrounding tunica albuginea and prepared for organ bath studies.

Preparation of compound stock solutions and dose responses. $PGE_1$ (Cayman Chemical Co., Ann Arbor, Mich.) is stored at −20° C. in solid form until the day of use. Stock solutions are made by adding 1 ml of 70% DMSO to a vial containing 1 mg of $PGE_1$. Compounds of the invention are dissolved in 1 ml of 70% DMSO, divided into 100 µl aliquots and stored at −20° C. until use. For dose responses in organ baths, stock solutions of $PGE_1$ and compounds of the invention are diluted with 70% DMSO to make the highest concentration and then serially diluted with 2% DMSO for all other doses. In a typical dose response curve, the concentration of DMSO is checked to remain below 0.1% in the 25 ml bath and to not exceed 0.5% at the highest dose.

Organ bath studies. Human or rabbit cavernosal tissue strips are mounted onto a fixed support with silk ties and attached to a tension transducer (model FT03; GrassTelefactor, Astro-Med, Inc. West Warwick, R.I.) with a rigid metal wire. After mounting, tissue strips are immersed in 25 ml baths of physiologic salt solution (PSS; 118.3 mM NaCl, 4.7 mM KCl, 0.6 mM $MgSO_4$, 1.2 mM $KH_2PO_4$, 2.5 mM $CaCl_2$, 25 mM $NaHCO_3$, 0.026 mM $CaNa_2EDTA$, 11.1 mM glucose). The solution is gassed with 95% air/5% $CO_2$ to attain a pH of 7.4 and the temperature is maintained at 37° C. All tissue strips are treated with 3 µM indomethacin to inhibit endogenous prostanoid production and minimize spontaneous contractile activity. The corpus cavernosum tissue is stretched incrementally and the optimal resting isometric tension for contraction is determined. After every 3-4 stretches (1 g tension/stretch), the tissue is contracted with 1 µM phenylephrine. When the amplitude of the phenylephrine-induced contraction is within 10% of the previous contraction, that tension is considered optimal for isometric contraction. All tissue strips are extensively washed with fresh PSS. Tissue strips are then contracted with 1 µM phenylephrine. After stable tone is achieved, tissue strips are exposed to increasing concentrations of $PGE_1$ or compounds of the invention.

Data analysis. At the end of each experiment, all tissue strips are treated with 10 µM papaverine and 10 µM nitroprusside to induce maximal relaxation (100%). The total amount of relaxatory response over the range of drug concentrations tested is determined by the area under the plotted curves. $EC_{50}$ values are calculated using Prism software (GraphPad, San Diego, Calif.). For final analysis of data, relaxation parameters are compared using ANOVA. If the ANOVA p-value is less than 0.05, paired post-test comparisons is carried out using the Tukey-Kramer test.

Table 2 summarizes results of the organ bath studies. Compound #1 caused a dose-dependent relaxation of human penile cavernosal tissue strips after contraction with phenylephrine. DP receptor agonist BW245C (reference molecule) caused relaxation with comparable potency ($EC_{50}$=59 nM).

However, the extent of relaxation (maximal effect) was greater for compound #1 than for BW245C. Both compounds were more potent than $PGE_1$ ($EC_{50}$=210 nM). $PGE_1$ is currently used for men who are unresponsive to PDE5 inhibitors. The endogenous DP receptor agonist $PGD_2$ caused dose-dependent relaxation of human cavernosal tissue through 0.3 μM, but caused contraction at higher concentration. This response profile formed the rationale for further in-vivo evaluation of DP agonists in animals.

TABLE 2

Relaxation of human penile cavernosal tissue strips after contraction with phenylephrine

| Compound | $EC_{50}$ [nM] |
|---|---|
| #1 | 29 nM |
| BW 245C | 59 nM |
| $PGE_1$ | 210 nM |
| $PGD_2$ | 0.3 |

In Vivo Experiments (Rabbit): Intracavernosal Injection

DP agonists were solubilized in 40% propylene glycol and administered by intracavernosal injection to deliver the indicated dose in 0.1 ml total volume. Since penile intracavernosal pressure (ICP) is ultimately limited by the systemic arterial pressure (SAP), all erectile responses were normalized by calculating the ration of ICP/SAP.

In rabbits, intracavernosal injections of compound #1 caused either sustained periods of penile tumescence or transient episodes that lasted 1-3 minutes. The arterial pressure remained constant. In one rabbit, repeated and transient episodes of spontaneous penile tumescence were recorded after intracavernosal administration of highest dose (5 μg) of compound #1. In a separate animal, intracavernosal injection of highest dose (5 μg) of compound #1 resulted in the recordal of arterial pressure waves that were clearly transmitted into the cavernosal compartment, indicating that the penile resistance arteries were fully dilated. Compared to vehicle (40% propylene glycol), compound #1 consistently caused dose-dependant increases in the ICP/SAP, as determined by the peak response or the "area-under the curve" (AUC). Similar pro-erectile responses were also observed in rats. Intracavernosal injection of BW245C in rats resulted in similar pro-erectile activity to compound #1. In rabbits no overt changes in systemic blood pressure were noted after administration of any dose of compound #1. All data suggest that DP1 receptors mediate cavernosal smooth muscle relaxation in multiple species and that intracavernosal administered compound #1 is a potent agonist that shows efficacious activity in initiating erections in humans.

Currently, $PGE_1$ is used for men who are unresponsive to PDE5 inhibitors either because extent of local penile tissue damage or because neural damage prevents use of PDE5 inhibitors as a therapeutic option. However, $PGE_1$ causes local fibrotic responses with injection, leading to a gradually increasing severity of cavernosal fibrosis and further dysfunction. Therefore, compound #1 may be used as a useful alternative to intracavernosal injections of prostaglandin E1 ($PGE_1$).

5.7 In Vivo Effect on Bone Loss Prevention

The activity of compounds of the invention as a bone anabolic agent can be tested for example in a rat ovariectomy model such as follows. Virgin female Sprague Dawley rats are randomized into treatment groups based on pre-dose body weight measurements. The aim is to achieve approximately the same average body weight for every treatment group.

Surgery: Animals are sedated with ketamine and xylazine (SOP ST-AEP007). The hair on the dorsal abdominal surface is shaved and prepped for aseptic surgery. A single incision is made along the midline, starting just anterior to the lumbar region of the spine. The underlying musculature on both sides of the dorso-lateral region of the abdomen is exposed. An incision is made through the musculature to gain access to the abdominal cavity.

For a group of animals ("Ovx"), the ovary is located and cut at the junction of the uterine horn and removed. The uterus is replaced and the muscles sutured. Repeat on the contra-lateral side.

For a control group of animals ("Sham"), the ovaries are located and exteriorized, but not removed. The uterus and ovaries are replaced into the abdominal cavity and the muscles sutured.

The muscle layers are closed with suture and the skin incision closed using wound clips.

Dosing: Dosing is commenced one day after the surgery is performed. The animals receive daily subcutaneous injections for 6 weeks following surgery. The doses of 0.1, 1.0, 10.0 mg/kg of compounds of the invention are used. A control group receives daily subcutaneous injections of 17 βestradiol (Sigma Chemicals) of 30 μg/kg for 6 weeks following surgery. Control groups of animal (the "sham" group and an "Ovx" group) are injected s. c. vehicle (saline).

Fluorochrome Labels: To enable the performance of dynamic histomorphometry, two injections of calcein (10 mg/kg, i. p.) are given 6 and 2 days prior to the necropsy.

Body Weights and Clinical Observations: Body weights are recorded weekly, beginning one week prior to the commencement of treatment and continuing until the conclusion of the treatment period. In addition, the rats are observed daily for signs of ill health or reaction to treatment.

Blood and Urine Biochemistry: An eighteen-hour urine specimen is collected from each animal prior to the sacrifice using metabolic cages. At sacrifice, blood samples are collected from each rat, under inhalation anesthesia (ether) from the retro-orbital sinus. Following parameters are measured in urine and serum.

Parameter Method: Urinary deoxypyridinoline is measured by Immuno-assay (Pyrilinks-D Quidel, Mt. View, Calif.); Urinary creatinine is measured by COBAS chemistry instrument (Creatinine Reagent Roche Diagnostics, Indianapolis, Ind.); Serum osteocalcin is measured by Immuno-assay (Rat OSU IRMA, Immunotopics San Clemente, Calif.).

Necropsy: Upon completion of dosing and urine/blood collection, animals are euthanized using carbon dioxide asphyxiation. All animals are subjected to the following procedure. Terminal body weights are recorded. A gross examination is performed and a check for abnormalities is performed. The following investigation are performed, as detailed:

Bone Mineral Density Scans: L2-L4 lumbar vertebrae is subjected to DXA (Dual-energy X-ray absorptiometry) scan using aPIXImus instrument (Lunar Corp. Madison, Wis.). Bone mineral content, area and density are determined from the PIXI scan. Bone mineral density measurements by DXA are described in Formica et al. 1998, Osteoporosis International, 8 (5), 460-467.

Right femur is subject to pQCT (peripheral quantitative computed tomography) scan using a Stratec XCT RM and associated software (StratecMedizinteclmik Gmbh, Pforzheim, Germany. Software version 5.40 C). The femur is scanned at two sites, 20% of the distal femur and 50% of the mid-femur. The position is verified using scout views and scan results from one 0.5 mm slice perpendicular to the long axis of the femur shaft is recorded. Total bone mineral content, total bone area, total bone mineral density, trabecular bone mineral content, trabecular bone area and trabecular bone mineral density are analyzed from the scan of the distal femur. For the midshaft femur, total bone mineral content, total bone area, total bone mineral density, cortical bone mineral content, cortical bone area, cortical bone mineral density, periosteal perimeter and endosteal perimeter are analyzed.

Bone mineral density measurements by pQCT are described in Formica et al. 1998, Osteoporosis International, 8 (5), 460-467 and in Tsugeno 2002, Osteoporosis International 13(8), 650-656.

Biomechanical Testing of Lumbar Vertebrae and Femurs: L5 Lumbar vertebra is isolated from L5-L6 and prepared for mechanical testing by removing the vertebral arch and pedicle using a low-speed diamond saw. The cranial and caudal ends of each vertebral body are also removed to produce a vertebral body specimen with two parallel surfaces and a height of approximately 4 mm. The width of the vertebral body in the medial-lateral and anterior-posterior directions is measured using electronic digital calipers. These values are recorded and used in the calculation of cross-sectional area. The height of the vertebral body specimen is also taken with an electronic caliper and recorded. The specimens are then placed between two platens and load applied at a displacement rate of 6 mm/min until failure in an Instron Mechanical Testing Instrument (Instron 4465, retrofitted to 5500).

The load and displacement are recorded by: Instron Instrument Software (Merlin II, Instron) and the locations for maximum load at failure, stiffness and energy absorbed are selected manually from the load and displacement curve. The intrinsic properties, stress, elastic modulus and toughness are then calculated from maximum load, stiffness, energy absorbed, cross-sectional area, and height.

After the pQCT scan, the anterior to posterior diameter at the midpoint of the femoral shaft is taken with an electronic caliper and recorded. Femur is then placed on the lower supports of a three point bending fixture with anterior side facing downward in an Instron Mechanical Testing Instrument (Instron 4465, retrofitted to 5500). The span between the two lower supports is set at 14 mm. The upper loading device aligned to the center of the femoral shaft. The load is applied at a constant displacement rate of 6 mm/min until the femur breaks. The locations of maximal load, stiffness and energy absorbed are selected manually and values calculated by instrument's software (Merlin II, Instron). The intrinsic properties, stress, elastic modulus and toughness are calculated from maximum load, stiffness, energy absorbed, anterior-posterior diameter, and moment of inertia.

After the three point bending test, a 3-mm segment of the distal femoral metaphysis is cut directly proximal to the femoral condyle with a low-speed diamond saw. The load is applied with a cylindrical indenter (with a flat testing face of 1.6 mm diameter (d)) to the center of marrow cavity on the distal face of the segment. The indenter is allowed to penetrate the cavity at a constant displacement rate of 6 mm/min to a depth of 2 mm before load reversal. The locations of maximum load, stiffness and energy absorbed is selected manually from load displacement curve and then calculated by the instrument's software (Merlin II, Instron). Stress is calculated by dividing the maximum load by the indenter area.

Bone Histology and Dynamic Histomorphometry:

Dehydration, embedding and sectioning Formalin-fixed samples of proximal tibia are dehydrated in a series of ascending ethanol concentration. Following dehydration, bone samples are infiltrated and embedded in methyl methacrylate-based plastic. Embedded samples of the proximal tibia are sectioned longitudinally using a Leitz motorized rotary microtome equipped with a tungsten-carbide microtome knife. Once the blocks are trimmed, 4 µm sections are stained with Goldner's trichrome stain for microscopy. The 8 µm sections are left unstained for epifluorescence microscopy.

Histomorphometric Determinations

Static and dynamic histomorphometry of the proximal tibia is performed. The measurement includes the secondary spongiosa (area that is 1.05 from the lowest point of the growth plate).

Bone histomorphometry is performed using an OsteoMeasure software program (OsteoMetrics, Inc. Atlanta, Ga.) interfaced with a Nikon Eclipse E400 light/epifluorescent microscope and video subsystem. Histomorphometry is read in a blinded manner. Total tissue area, trabecular bone area, trabecular bone perimeter, and osteoclast perimeter is measured on 4 µm thick Goldner's trichrome stained sections. Percent trabecular bone area, trabecular number, trabecular thickness, trabecular separation and osteoclast perimeter as a percentage of bone surfaces are then calculated according to standardized formulae. For dynamic parameters, single-labeled calcein perimeter, double-labeled calcein perimeter, and interlabel width (label thickness) is measured on 8 µm thick unstained sections, and the mineralizing surface, mineral apposition rate, bone formation rate-surface referent is calculated.

5.8 In Vivo Effect on Adjuvant Induced Arthritis in Rats

The compounds also may be monitored for their efficacy against adjuvant-induced arthritis in rats. In an exemplary such assay, female Lewis rats (body weight about 146-170 g) are weighed, ear marked, and assigned to groups (a negative control group in which arthritis is not induced, a vehicle control group, a positive control group administered indomethacin at a total daily dose of 1 mg/kg and four groups administered with a test compound at total daily doses of 0.10-3.0 mg/kg) such that the body weights are equivalent within each group. Six groups of 10 rats are each injected into a hind paw with 0.5 mg of Mycobacterium butyricum in 0.1 mL of light mineral oil (adjuvant), and a negative control group of 10 rats that has not been injected with adjuvant. Body weights, contralateral paw volumes (determined by mercury displacement plethysmography) and lateral radiographs (obtained under Ketamine and Xylazine anesthesia) are determined before (day-1) and 21 days following adjuvant injection, and primary paw volumes are determined before (day-1) and on days 4 and 21 following adjuvant injection. The rats are anesthetized with an intramuscular injection of 0.03-0.1 mL of a combination of Ketamine (87 mg/kg) and Xylazine (13 mg/kg) for radiographs and injection of adjuvant. The radiographs are made of both hind paws on day 0 and day 21 using the Faxitron (45 kVp, 30 seconds) and Kodak X-OMAT TL film, and are developed in an automatic processor. Radiographs are evaluated for changes in the soft and hard tissues by an investigator who is preferably blinded to experimental treatment. The radiographic changes may be graded numerically according to severity e.g., increased soft issue volume (0-4), narrowing or widening of joint spaces (0-5) subehondral erosion (0-3), periosteal reaction (0-4), osteolysis (0-4) subluxation (0-3), and degenerative joint changes (0-3). Specific criteria can be used to establish the numerical grade of severity for each radiographic change. The maximum possible score per foot may be set at a value determined by the investigator, e.g., 26. A test compound at total daily doses of 0.1, 0.3, 1, and 3 mg/kg/day, indomethacin at a total daily dose of 1 mg/kg/day, or vehicle (0.5% methocel in sterile water) are then administered per os b.i.d. beginning post injection of adjuvant and continuing for 21 days. The compounds are prepared weekly, refrigerated in the dark until used, and vortex mixed immediately prior to administration.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. A compound of the Formula I

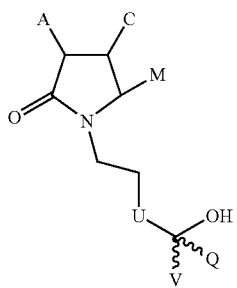

or a pharmaceutically acceptable salt thereof;
wherein: A and C are hydrogen;
M is selected from the group consisting of optionally substituted $C_1$-$C_7$ alkyl, $C_2$-$C_6$ alkenyl, $C_2$-$C_6$ alkynyl and —$(CH_2)$q-B;
wherein B is selected from the group comprising optionally substituted carbocyclic aryl, optionally substituted heteroalicyclic having from 3 to 8 ring atoms and at least one N, O or S ring atom and a heteroaromatic group having a single ring with 5 or 6 ring atoms and at least one N, O or S ring atom;
wherein q in "—$(CH_2)$q-B" is selected from 1, 2, 3 and 4;
U is $(CH_2)_p$ wherein p is selected from 0, 1 and 2; and
V and Q are each independently hydrogen, optionally substituted alkyl, or $C_3$-$C_6$ cycloalkyl;
with at least one of V and Q being other than hydrogen.

2. The compound of claim 1, wherein B is optionally substituted carbocyclic aryl.

3. The compound of claim 1, wherein B is optionally substituted phenyl.

4. A compound of claim 1, according to Formula II:

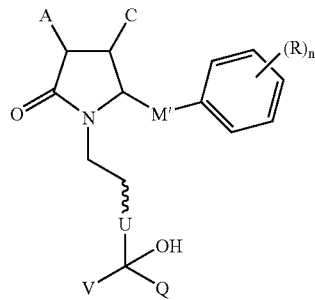

or a pharmaceutically acceptable salt thereof;
wherein M' is selected from the group consisting of: optionally substituted $C_1$-$C_7$ alkyl, $C_2$-$C_6$ alkenyl, and $C_2$-$C_6$ alkynyl;
R is C(=O)Z where Z is selected from hydrogen, hydroxy, optionally substituted alkoxy and optionally substituted alkyl; or R is amino or optionally substituted alkylamine;
n is an integer selected from 0, 1, 2, 3, 4 and 5;
U is $(CH_2)_p$;
p is selected from 0, 1 and 2;
V and Q are each independently hydrogen or optionally substituted alkyl;
with at least one of V and Q being other than hydrogen.

5. The compound of claim 4, wherein n is 1 or 2.

6. A compound of claim 1, according to Formula III:

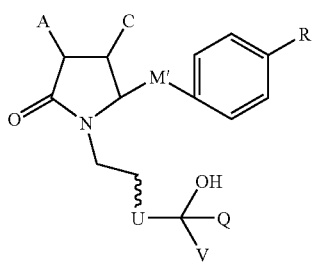

or a pharmaceutically acceptable salt thereof;
wherein M' is selected from the group consisting of: optionally substituted $C_1$-$C_7$ alkyl, $C_2$-$C_5$ alkenyl, and $C_2$-$C_6$ alkynyl;
R is C(=O)Z where Z is selected from hydrogen, hydroxy, optionally substituted alkoxy and optionally substituted alkyl; or R is amino or optionally alkylamine;
U is $(CH_2)_p$;
p is selected from 0, 1 and 2;
V and Q are each independently hydrogen or optionally substituted alkyl;
with at least one of V and Q being other than hydrogen.

7. The compound of claim 1, according to Formula IV:

![Formula IV structure]

or a pharmaceutically acceptable salt thereof;
wherein M' is selected from the group consisting of:
  optionally substituted $C_1$-$C_7$ alkyl, $C_2$-$C_6$ alkenyl, and $C_2$-$C_6$ alkynyl;
R is C(=O)Z; where Z is selected from hydrogen, hydroxy, optionally substituted alkoxy and optionally substituted alkyl; or R is amino or optionally substituted alkylamine;
n is an integer selected from 0, 1, 2, 3, 4 and 5;
U is $(CH_2)_p$;
p is selected from 0, 1 and 2;
Q is hydrogen or optionally substituted alkyl or $C_3$-$C_6$ cycloalkyl.

8. The compound according to claim 7, wherein:
Q is an optionally substituted $C_1$-$C_{12}$ alkyl, or $C_3$-$C_6$ cycloalkyl.

9. The compound according to claim 1, wherein p is zero.

10. The compound of claim 4, wherein p is zero.

11. The compound of claim 6, wherein p is zero.

12. The compound of claim 7, wherein p is zero.

13. A compound of claim 1, according to Formula V:

![Formula V structure]

or a pharmaceutically acceptable salt thereof;
wherein M' is selected from the group consisting of:
  optionally substituted $C_1$-$C_7$ alkyl, $C_2$-$C_6$ alkenyl, and $C_2$-$C_6$ alkynyl;
R is C(=O)Z; where Z is selected from hydrogen, hydroxy, optionally substituted alkoxy and optionally substituted alkyl; or R is amino or optionally substituted alkylamine;
n is an integer selected from 0, 1, 2, 3, 4 and 5;
Q is optionally substituted alkyl, or $C_3$-$C_6$cycloalkyl.

14. The compound of claim 13, wherein n is 1 and R is a para-substituent.

15. The compound of claim 13 wherein R is —C(O)OH.

16. The compound of claim 13, wherein Q is a straight or branched $C_1$-$C_{12}$ alkyl.

17. The compound of claim 13 wherein:
R is —C(O)OH is in a "para" position and n is 1.

18. The compound of claim 1, wherein M has the formula:

![M formula structure]

wherein M' is selected from the group consisting of:
  optionally substituted $C_1$-$C_7$ alkyl, $C_2$-$C_6$ alkenyl, and $C_2$-$C_6$ alkynyl;
A is selected from the group consisting of: optionally substituted pyridyl, pyrrolyl, furyl (furanyl), thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl and benzoquinolyl; and
R is C(=O)Z where Z is selected from hydrogen, hydroxy, optionally substituted alkoxy and optionally substituted alkyl; or R is amino or optionally substituted alkylamine; n is an integer selected from 0, 1, 2, 3, 4 and 5.

19. The compound of claim 1, wherein M is selected from the group consisting of:

![Series of M group structures showing various substituted aryl/heteroaryl and alkenyl carboxylic acid moieties]

20. The compound of claim 1, wherein M is selected from the group consisting of:

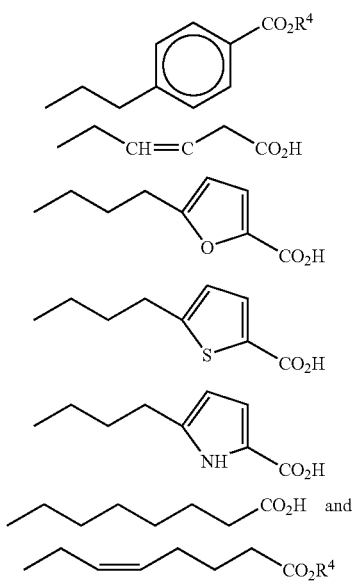

wherein R⁴ is selected from the group consisting of: H, an alkyl group, and an aryl group or a salt.

21. The compound of claim 1, wherein M is:

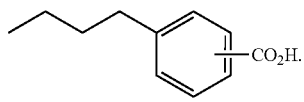

22. The compound of claim 1, wherein M is:

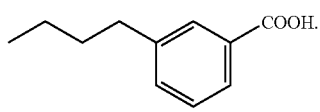

23. The compound of claim 1, wherein M is:

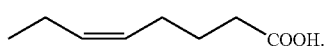

24. A compound selected from the group consisting of:
4-(3-(2S)-1-[(3R)-3-cyclohexyl-3-hydroxypropyl]-5-oxotetrahydro-1H-2-pyrrolylpropyl)benzoic acid;
4-(3-(2S)-1-[(3S)-3-cyclohexyl-3-hydroxypropyl]-5-oxotetrahydro-1H-2-pyrrolylpropyl)benzoic acid;
7-{(2S)-1-[(3R)-3-cyclohexyl-3-hydroxypropyl]-5-oxopyrrolidin-2-yl}Heptanoic acid; and
7-{(2S)-1-[(3R)-3-cyclohexyl-3-hydroxypropyl]-5-oxopyrrolidin-2-yl}Heptanoic acid, or a pharmaceutically acceptable salt thereof.

25. A compound according to formulae I2, II2, III2, IV2, V2, and V3, as shown below:

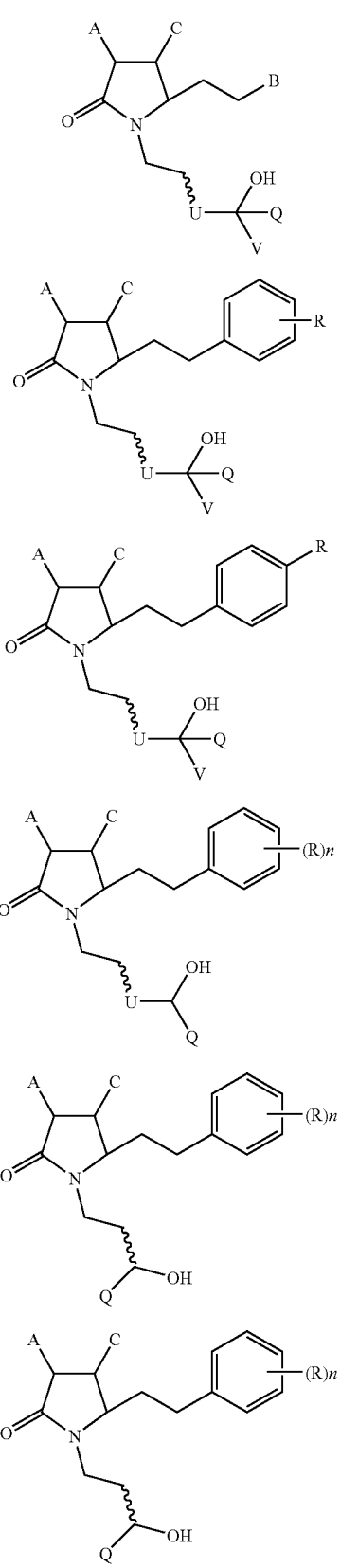

or a pharmaceutically acceptable salt thereof;

wherein A and C are hydrogen;

B is selected from the group comprising: optionally substituted carbocyclic aryl, optionally substituted heteroalicyclic having from 3 to 8 ring atoms and at least one nitrogen, oxygen or sulfur ring atom, and a heteroaromatic group having a single ring with 5 or 6 ring atoms and at least one nitrogen, oxygen, or sulfur ring atom;

R is C(=O)Z where Z is selected from hydrogen, hydroxy, optionally substituted alkoxy and optionally substituted alkyl; or R is amino or optionally substituted alkylamine;

n is an integer selected from 0, 1, 2, 3, 4 and 5;

U is $(CH_2)_p$;

p is selected from 0, 1 and 2;

V and Q are each independently hydrogen, optionally substituted alkyl or $C_3$-$C_6$ cycloalkyl;

with at least one of V and Q being other than hydrogen.

26. A pharmaceutical composition comprising a compound according to claim 1 and a pharmaceutically acceptable carrier.

27. A method of treatment of a mammal suffering from a disease or disorder associated with prostaglandin deficiency, wherein the disease or disorder is chosen from: erectile dysfunction, asthma, and sexual dysfunction, comprising administering to said mammal an effective amount of a compound according to Formula I:

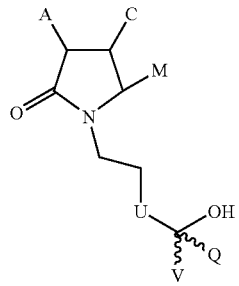

I or a pharmaceutically acceptable salt thereof:

wherein: A and C are hydrogen;

M is selected from the group consisting of optionally substituted $C_1$-$C_7$ alkyl, $C_2$-$C_6$ alkenyl, $C_2$-$C_6$ alkynyl and —$(CH_2)$q-B;

wherein B is selected from the group comprising: optionally substituted carbocyclic aryl, optionally substituted heteroalicyclic having from 3 to 8 ring atoms and at least on N, O or S ring atom, and a heteroaromatic group having a single ring with 5 or 6 ring atoms and at least on N, O or S ring atom;

wherein q in "—$(CH_2)_q$-B" is selected from 1, 2, 3, and 4;

U is $(CH_2)_p$ wherein p is selected from 0, 1 and 2;

V and Q are each independently hydrogen, optionally substituted alkyl or $C_3$-$C_6$ cycloalkyl with at least one of V and Q being other than hydrogen.

28. The method of claim 27, wherein the disease is chosen from: preterm labor, dysmenorrhea, asthma, hypertension, a fertility disorder, undesired blood clotting, preeclampsia, eclampsia, an eosinophil disorder, undesired bone loss, sexual dysfunction, renal dysfunction, an immune deficiency disorder, dry eye, ichthyosis, elevated intraocular pressure, a sleep disorder, a gastric ulcer, inflammatory disorder and erectile dysfunction.

29. The method of claim 28, wherein the disease is erectile dysfunction.

30. The method of claim 29, wherein the compound is administered by intracavernosal injection.

* * * * *

UNITED STATES PATENT AND TRADEMARK OFFICE
CERTIFICATE OF CORRECTION

PATENT NO. : 7,696,243 B2
APPLICATION NO. : 11/791882
DATED : April 13, 2010
INVENTOR(S) : Gian Luca Araldi Page 1 of 1

It is certified that error appears in the above-identified patent and that said Letters Patent is hereby corrected as shown below:

Column 60, line 56 (Claim 6), "$C_1$-$C_7$ alkyl, $C_2$-$C_5$ alkenyl"
should read --$C_2$-$C_6$ alkenyl--

Column 66, line 22 (Claim 28), "The method of claim 27, wherein the disease is chosen from: preterm labor, dysmenorrhea, asthma, hypertension, a fertility disorder, undesired blood clotting, preeclampsia, eclampsia, an eosinophil disorder, undesired bone loss, sexual dysfunction, an immune deficiency disorder, dry eye, ichthyosis, elevated intraocular pressure, a sleep disorder, a gastric ulcer, inflammatory disorder and erectile dysfunction."
should read --The method of claim 27, wherein the mammal is a male.--

Signed and Sealed this

Third Day of August, 2010

David J. Kappos
*Director of the United States Patent and Trademark Office*